(12) United States Patent
Suzuki et al.

(10) Patent No.: US 7,485,755 B2
(45) Date of Patent: Feb. 3, 2009

(54) ACID ADDITION SALT OF CARBASUGAR AMINE DERIVATIVE

(75) Inventors: Kiyoshi Suzuki, Tokyo (JP); Masami Iida, Kanagawa (JP); Yuji Kaneda, Tokyo (JP); Naoko Kajimoto, Tokyo (JP); Miwa Sawa, Saitama (JP)

(73) Assignee: Seikagaku Corporation, Tokyo (JP)

( * ) Notice: Subject to any disclaimer, the term of this patent is extended or adjusted under 35 U.S.C. 154(b) by 0 days.

(21) Appl. No.: 10/557,851

(22) PCT Filed: May 19, 2004

(86) PCT No.: PCT/JP2004/007138

§ 371 (c)(1), (2), (4) Date: Nov. 21, 2005

(87) PCT Pub. No.: WO2004/101493

PCT Pub. Date: Nov. 25, 2004

(65) Prior Publication Data

US 2007/0010585 A1    Jan. 11, 2007

(30) Foreign Application Priority Data

May 19, 2003    (JP)    ............................. 2003-140868

(51) Int. Cl.
C07C 211/40    (2006.01)
A61K 31/13    (2006.01)

(52) U.S. Cl. ...................... 564/462; 514/659

(58) Field of Classification Search ....................... None
See application file for complete search history.

(56) References Cited

U.S. PATENT DOCUMENTS 4,486,602 A * 12/1984 Horii et al. .................. 564/360
2004/0225015 A1 * 11/2004 Ogawa et al. ............... 514/579

FOREIGN PATENT DOCUMENTS

| EP | 0 049 981 A1 | 4/1982 |
|----|---|---|
| EP | 1 433 776 A1 | 6/2004 |
| JP | 57-64648 | 4/1982 |
| JP | 96/39412 | 12/1996 |
| WO | 03/022797 | 3/2003 |

OTHER PUBLICATIONS

Database CAPLUS on STN, Acc. No. 2003:221644, Ogawa et al., WO 2003022797 (Mar. 20, 2003) (abstract).*
Seiichiro Ogawa, et al., "Chemical Modification of the β-Glucocerebrosidase Inhibitor N-Octyl-β-valienamine: Sythesis and Biological Evaluation of 4-Epimeric and 4-O-(β-D-Galactopyranosyl) Derivatives", Bioorganic & Medicinal Chemistry, XP-002960728, No. 10, 2002, pp. 1967-1972.
Seiichiro Ogawa, et al., Synthesis of Potent β-D-Glucocerebrosidase Inhibitors: N-Alkyl-β-Valienamines, Bioorganic & Medicinal Chemistry Letters, vol. 6, No. 8, 1996, pp. 929-932.

* cited by examiner

*Primary Examiner*—Brian J Davis
(74) *Attorney, Agent, or Firm*—Oblon, Spivak, McClelland, Maier & Neustadt, P.C.

(57) ABSTRACT

An acid addition salt of a carba-sugar amine derivative represented by the following formula (1):

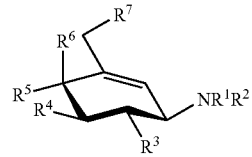

(1)

wherein $R^1$ and $R^2$ each independently represents a hydrogen atom, or an alkyl group, an alkenyl group, an alkynyl group, an acyl group, an aryl group or an aralkyl group which may have one or at least two of the following substituent (I) or (II), or $R^1$ and $R^2$ are taken together to represent a substituent (III)

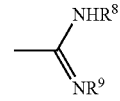

(I)

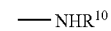

(II)

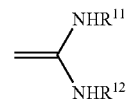

(III)

($R^8$ to $R^{12}$ each independently represents an alkyl group, an alkenyl group, an alkynyl group, an acyl group, an aryl group or an aralkyl group), with the proviso that both $R^1$ and $R^2$ are not a hydrogen atom at the same time; $R^3$, $R^4$ and $R^7$ each independently represents a hydroxyl group or a hydroxyl group having a substituent; and $R^5$ and $R^6$ each independently represents a hydrogen atom, or a hydroxyl group or a hydroxyl group having a substituent, with the proviso that when one of $R^5$ and $R^6$ is a hydrogen atom, the other is a hydroxyl group or a hydroxyl group having a substituent.

27 Claims, 7 Drawing Sheets

ACID ADDITION SALT OF CARBASUGAR AMINE DERIVATIVE

TECHNICAL FIELD

The present invention relates to acid addition salts of novel carba-sugar amine derivatives.

BACKGROUND OF THE INVENTION $G_{M1}$ gangliosidosis, ceramide lactoside lipidosis, Morquio B disease, Krabbe disease, Fabry disease, Gaucher disease, Tay-Sachs disease, Sandhoff disease, fucosidosis and the like are conventionally known as glycolipid metabolic disorders. These diseases are diseases which are generated as a result of causing mutation in various glycolytic enzymes. Among them, $G_{M1}$ gangliosidosis, Morquio B disease, ceramide lactoside lipidosis and Krabbe disease are diseases which are generated when β-galactosidase loses its enzyme activity by undergoing mutation, and Gaucher disease is a disease generated when β-glucosidase loses its enzyme activity by undergoing mutation Carba-sugar amine derivative are known as substances which have a possibility of becoming medicaments for these diseases (International Publication WO 03/022797).

The carba-sugar amine derivatives described in International Publication WO 03/022797 have a function to recover reduced or lost activity of a mutated enzyme, but being considerably low in their solubility in water, it could not be said that they are sufficient for using as medicaments.

DISCLOSURE OF THE INVENTION

In order to solve the above-described problems, the present inventors have conducted intensive studies and, as a result, discovered an acid addition salt of a specified carba-sugar amine derivative having strong β-galactosidase inhibitory activity or β-glucosidase inhibitory activity, and have found that this has excellent solubility in aqueous solvents, thus accomplishing the invention.

That is, the present invention relates to the followings:

(1) An acid addition salt of a carba-sugar amine derivative represented by the following formula (1):

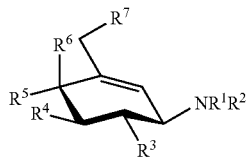

wherein $R^1$ and $R^2$ each independently represents a hydrogen atom, or an alkyl group, an alkenyl group, an alkynyl group, an acyl group, an aryl group or an aralkyl group which may have one or at least two of the following substituent (I) or (II), or $R^1$ and $R^2$ are taken together to represent a substituent (III):

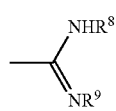

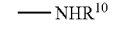

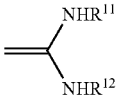

wherein $R^8$ to $R^{12}$ each independently represents an alkyl group, an alkenyl group, an alkynyl group, an acyl group, an aryl group or an aralkyl group;

with the proviso that both $R^1$ and $R^2$ are not a hydrogen atom at the same time;

$R^3$, $R^4$ and $R^7$ each independently represents a hydroxyl group or a hydroxyl group having a substituent; and $R^5$ and $R^6$ each independently represents a hydrogen atom, a hydroxyl group or a hydroxyl group having a substituent, with the proviso that when one of $R^5$ and $R^6$ is a hydrogen atom, the other is a hydroxyl group or a hydroxyl group having a substituent.

(2) An acid addition salt of a carba-sugar amine derivative represented by the following formula (1)-A-2:

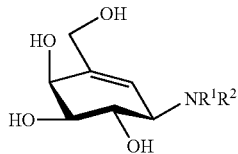

wherein $R^1$ and $R^2$ each represents as defined in the above-described (1).

(3) An acid addition salt of a carba-sugar amine derivative represented by the following formula (1)-B-2;

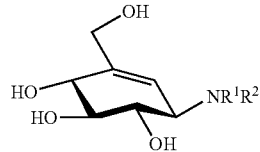

wherein $R^1$ and $R^2$ each represents as defined in the above-described (1).

(4) The acid addition salt of a carba-sugar amine derivative according to any one of (1) to (3), which is hydrochloride or sulfate.

(5) A medicament which comprises the acid addition salt of a carba-sugar amine derivative according to any one of (1) to (4) as an active ingredient.

(6) The medicament according to (5), which is a preventive agent or a therapeutic agent for glycolipid metabolic disorders.

(7) A process for producing an acid addition salt of a carba-sugar amine derivative, which comprises allowing a carba-sugar amine derivative represented by the following formula (1) to contact with an acid in an aqueous solvent to obtain the acid addition salt thereof:

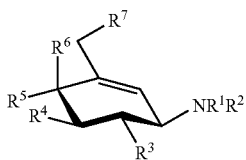
(1)

wherein $R^1$ and $R^2$ each independently represents a hydrogen atom, or an alkyl group, an alkenyl group, an alkynyl group, an acyl group, an aryl group or an aralkyl group which may have one or at least two of the following substituent (I) or (II), or $R^1$ and $R^2$ are taken together to represent a substituent (III):

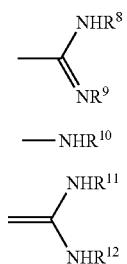

(I)
(II)
(III)

wherein $R^8$ to $R^{12}$ each independently represents an alkyl group, an alkenyl group, an alkynyl group, an acyl group, an aryl group or an aralkyl group;

with the proviso that both $R^1$ and $R^2$ are not a hydrogen atom at the same time;

$R^3$, $R^4$ and $R^7$ each independently represents a hydroxyl group or a hydroxyl group having a substituent; and $R^5$ and $R^6$ each independently represents a hydrogen atom, a hydroxyl group or a hydroxyl group having a substituent, with the proviso that when one of $R^5$ and $R^6$ is a hydrogen atom, the other is a hydroxyl group or a hydroxyl group having a substituent.

The present invention is described below in more detail based on the embodiments of the present invention.

The present invention relates to an acid addition salt of a carba-sugar amine derivative represented by the above-described formula (1) (hereinafter referred to as the "substance of the invention").

In this formula, $R^1$ and $R^2$ each independently represents a hydrogen atom, or a group generally used in the field of organic chemistry for modifying functional groups or protecting side chains, such as an alkyl group, an aryl group or an aralkyl group, which may have one or at least two of the following substituent (I) or (II), or $R^1$ and $R^2$ are taken together to represent a substituent (III):

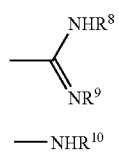

(I)
(II)

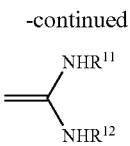

(III)

$R^8$ to $R^{12}$ each independently represents an alkyl group, an alkenyl group, an alkynyl group, an acyl group, an aryl group or an aralkyl group, wherein both $R^1$ and $R^2$ are not a hydrogen atom at the same time.

The above-described alkyl group includes linear or branched alkyl groups having from 1 to 30, preferably from 2 to 23 carbon atoms. Particularly, when a medicament comprising the substance of the present invention as the active ingredient (hereinafter referred to as the "medicament of the invention") is applied to a disease which is generated by an abnormality of a sphingoglycolipid metabolic system, it is preferable that the structure of the active ingredient can become a sphingoglycolipid analogue. That is, as a sphingoglycolipid analogue (a substance which has a structure similar to that of sphingoglycolipid and performs an action similar to or competitive with that of sphingoglycolipid) mainly existing in the living body, it is most desirable that $R^1$ in the above-described formula has a linear alkyl group particularly having from 8 to 23 carbon atoms.

Regarding the branched alkyl group among the above-described alkyl groups, a substituent may be introduced into the alkyl group, and examples of the substituent include an alkoxy group, an aryloxy group, an amino group, a hydroxy group, a silyl group and the like. In general, the branched alkyl group may have a structure in which, for example, a linear alkyl group (it may also be a branched alkyl group) is further bound by a ether bond to a backbone in which a hydrogen atom bound to a carbon of an alkyl group such as an alkyl glycerol is substituted with a hydroxyl group (cf, the following formula (2)) (m in the following structural formula is each independently an integer of from 0 to 30) or the like:

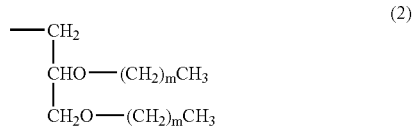

(2)

It is preferable that the above-described alkenyl group and alkynyl group have from 1 to 30, preferably from 2 to 23, carbon atoms, and they may have at least two carbon-to-carbon double bond or triple bond. The above-described acyl group may be any group, so long as it is a group generally represented by —CO—R, and the number of carbon atoms as a whole acyl group is from 1 to 30, preferably from 2 to 23. In this connection, R in the above-described formula is any group selected from the above-described alkyl group, alkenyl group and alkynyl group and the aryl group and aralkyl group described below.

Also, the above-described aryl group includes an aryl group having from 6 to 22, preferably from 6 to 14, carbon atoms, and examples include aromatic hydrocarbon residues such as a phenyl group or a naphthyl group, or aromatic hydrocarbon residues in which a substituent such as an alkyl group or an acyl group is further substituted with a hydrogen atom of the aromatic ring (e.g., tolyl group and the like).

The above-described aralkyl group is a group having a general structure of Ar—(CH$_2$)$_n$— in which a hydrogen atom of an alkyl group is substituted with an aryl group, and the above-described n is preferably from 1 to 30, more preferably from 2 to 23. Examples of the aralkyl group include a benzyl group, a phenetyl group, an α-methylbenzyl group and the like.

Examples of the above-described alkyl group, alkenyl group, alkynyl group, acyl group, aryl group or aralkyl group which may have (I) or (II) having the above-described substituent include compounds of the following (A) to (D), and examples of the compound having the substituent (III) in which R$^1$ and R$^2$ are combined include the following compounds.

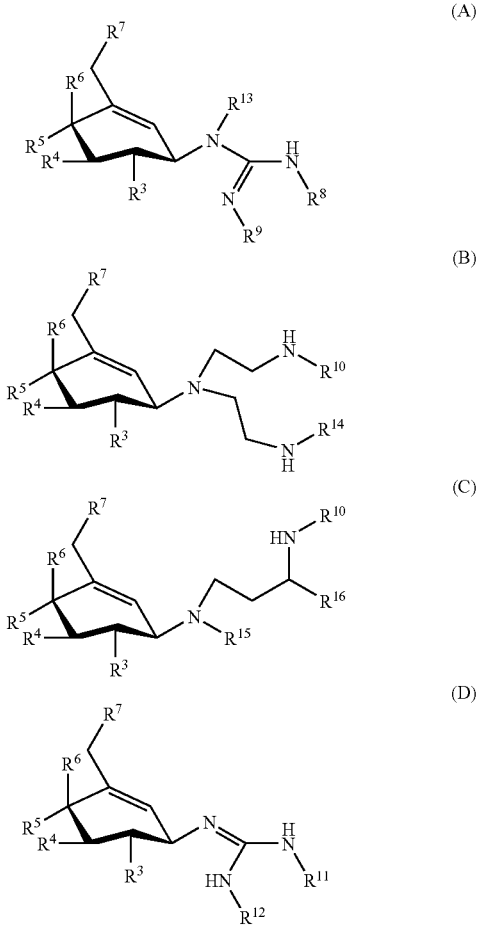

(In the formulae, R$^{13}$ to R$^{15}$ each represents a hydrogen atom, or an alkyl group, an alkenyl group, an alkynyl group, an acyl group, an aryl group or an aralkyl group having from 0 to 30 carbon atoms.)

When R$^3$, R$^4$ and R$^7$ each is a hydroxyl group or a hydroxyl group having a substituent, a hydroxyl group is particularly preferred.

However, when one of R$^5$ and R$^6$ is a hydroxyl group or a hydroxyl group having a substituent, the other is a hydrogen atom. Each of them is not a hydroxyl group nor hydroxyl group having a substituent at the same time. Also, when R$^5$ and R$^6$ each independently is a hydrogen atom, a hydroxyl group or a hydroxyl group having a substituent, hydroxyl group is particularly preferred.

In this connection, examples of the substituent of the hydroxyl group include single substituents such as aralkyl groups (benzyl group, phenetyl group, α-methylbenzyl group and the like), silyl groups (trimethylsilyl group, triethylsilyl group, triisopropylsilyl (TIPS) group, t-butyldiphenylsilyl (TBDPS) group, t-butyldimethylsilyl (TBDMS) group and the like), alkanoyl groups (acetyl group, butyryl group and the like), aroyl groups (benzoyl group, toluoyl group, naphthoyl group and the like), alkoxyalkyl groups (methoxymethyl (MOM) group and the like), and aralkyloxyalkyl groups (benzyloxymethyl (BOM) group and the like), and a group in which two of R$^3$ to R$^7$ together form a substituent such as alkylidene groups (methylidene group, ethylidene group and the like), an isopropylidene group and aralkylidene groups (benzylidene group and the like). Among these, MOM is particularly preferred from the viewpoint of its stability and easy handling and leaving.

When each of R$^3$, R$^4$, R$^6$ and R$^7$ is a hydroxyl group and R$^5$ is a hydrogen atom in a carba-sugar amine derivative represented by the above-described formula (I), it can be represented by the following formula (I)-A-2 (corresponding to Compounds 25-1 to 25-7 in FIG. 1).

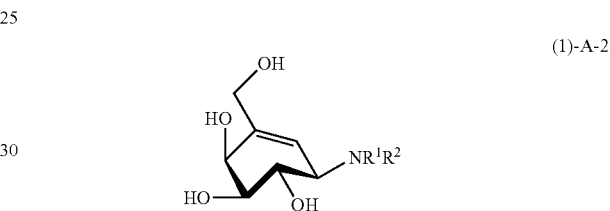

(I)-A-2

Also, when each of R$^3$, R$^4$, R$^5$ and R$^7$ is a hydroxyl group and R$^6$ is a hydrogen atom in a carba-sugar amine derivative represented by the above-described formula (I), it can be represented by the following formula (I)-B-2 (corresponding to Compounds 30-1 to 30-7 in FIG. 1).

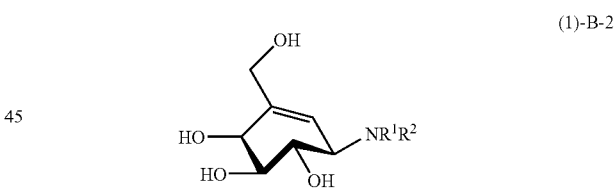

(I)-B-2

The substance of the invention is an acid addition salt of the compound represented by the above-described formula (I), and examples of such an acid addition salt include salts with acids such as inorganic acids (sulfuric acid, nitric acid, phosphoric acid, hydrohalogenic acids (hydrochloric acid, hypochlorous acid, hydrobromic acid and the like) and organic acids (acetic acid, propanoic acid, hydroxyacetic acid, 2-hydroxypropanoic acid, 2-oxopropanoic acid, ethanedioic acid, propanedioic acid, butanedioic acid, (Z)-butanedioic acid, (E)-2-butanedioic acid, 2-hydroxybutanedioic acid, 2,3-dihydroxybutanedioic acid, 2-hydroxy-1,2,3-propanetricarbonic acid, methanesulfonic acid, ethanesulfonic acid, benzenesulfonic acid, 4-methylbenzenesulfonic acid, toluenesulfonic acid, cyclohexanesulfamic acid, 2-hydroxybenzoic acid, 4-amino-2-hydroxybenzoic acid, oxalic acid, maleic acid, malonic acid, succinic acid, fumaric acid, mandelic acid, tartaric acid, malic acid, ascorbic acid, citric acid, lactic acid, butyric acid, salicylic acid, nicotinic acid and the like). Among these, inorganic acid salts are preferred, and hydrochloride or sulfate is particularly preferred.

In this connection, since the substance of the invention is an acid addition salt of the compound represented by formula (1) which is a kind of pseudo-sugar, carbon numbers of the compound in this description are described by the method shown in the following formula (3) in accordance with the case of hexose;

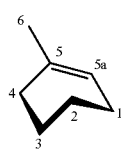

(3)

In addition, regarding the substituted amino group represented by $NR^1R^2$ in formula (1), when the substance of the invention as a pseudo-sugar is assumed to be a hexose (when, in the above-described formula (3), the carbon shown by 5a linked to the 1-position and 5-position is assumed to be the oxygen of the 6-membered ring), a case in which the substituted amino group ($NR^1R^2$) is on the upper side against the 6-membered ring is defined as β type, and is on the opposite side is defined as α type, and it is preferable that the substance of the invention is β type.

Since the substance of the invention is a salt of a substance having high inhibitory activity upon a β-galactosidase or β-glucosidase derived from a mammal, particularly human, it is possible to use the substance as a reagent which inhibits these enzymes in vitro or in vivo (cells, tissues and the like), a medicament based on such an enzyme inhibitory action or a medicament for treating (treating or preventing) glycolipid metabolic disorders. Since the substance of the invention has considerably higher solubility in water-soluble solvents, such as water, than that of the conventionally known free type substances, it is considered that its blood concentration can be increased and reduction of its dose can be attained when used particularly as a medicament, and preparation of various medicaments becomes easy. In addition, the substance of the invention can also be used in the studies on pathology of diseases induced by the mutation of β-galactosidase or β-glucosidase.

In this connection, the inhibitory activity upon β-galactosidase can be calculated by adding the substance of the invention to a solution containing β-galactosidase and its substrate, or to a solution containing β-glucosidase and its substrate in the case of the inhibitory activity upon β-glucosidase, and comparing the respective enzyme activities with the case of not adding the substance of the invention.

It is preferable that the substance of the invention is a salt of a substance having a 50% inhibition concentration ($IC_{50}$) of less than 1 μmol/l against the activity of mammalian β-galactosidase or β-glucosidase, and it is particularly preferable that the $IC_{50}$ is less than 0.5 μmol/l.

In addition, the substance of the invention can be synthesized by allowing a compound represented by the formula (1) (e.g., formula (1)-A-2 or (1)-B-2) obtained by the method described in International Publication WO 03/022797 or the synthesis route of FIG. 1 to react with, for example, 1 to 6 mol/l of an acid exemplified above (e.g., hydrochloric acid, acetic acid and the like) in an aqueous solvent. After the above-described reaction, the substance of interest can be obtained by a method in which this is azeotroped preferably with organic solvents (e.g., ethanol and toluene), and the residue is dissolved in water and freeze-dried.

The medicament of the invention may contain other components, so long as it contains an effective amount of the substance of the invention The medicament of the invention can be produced, for example, by combining the substance of the invention with a pharmaceutically acceptable carrier. Although the carrier is not particularly limited, examples include carriers which are generally used in medicaments such as excipients, binders, disintegrating agents, lubricants, stabilizing agents, correctives, diluents, surfactants, and solvents for injection.

Dosage forms of the medicament of the invention are not particularly limited and can be optionally selected in response to the therapeutic objects, and specific examples include tablets, pills, suspensions, emulsions, capsules, solutions, syrups, suppositories, injections, granules, powders, liposome forming agents, inhalation powders and the like.

The medicament of the invention can be administered orally or parenterally to mammals including human. The administration period is not particularly limited, and it is possible to select the administration period optionally in response to the therapeutic method of diseases to be treated. In addition, it is preferable to decide the administration form in response to the preparation forms, age, sex and other conditions of each patient, degree of symptoms of each patient and the like. Dose of the medicament of the invention is not particularly limited and should be individually set depending on the kind and specific activity of the active ingredient, the kind, symptoms and the like of the animal to be administered, and the kind of living body tissue to be administered and its conditions and the like, but in general, approximately from 0.1 μg to 1,000 mg can be administered per day as an acid addition salt of the compound represented by the formula (1).

Concentration of the active ingredient in the medicament of the invention is optionally selected in response to the usage, the age and sex of each patient, degree of the disease, other conditions and the like. In general, it is preferable that the concentration of the medicament of the invention is set to a range of from 0.001 to 5% (w/v) as the active ingredient. For example, when the medicament of the invention is used as solutions for oral administration, it is preferably 0.01% (w/v) or more, most preferably from 0.03% to 0.2% (w/v). Also, when used as injections for intramuscular injection or intravenous injection, it is preferably 0.01% (w/v) or more, most preferably 0.03% (w/v) or more.

Since the substance of the invention has a specific and strong inhibitory activity for normal β-galactosidase or β-glucosidase derived from a mammal and also has a function to restore activities of these enzymes reduced or lost in the living body, it can be used for the excellent treatment or prevention of glycolipid metabolic disorders based on the mutation of the β-galactosidase or β-glucosidase gene.

BEST MODE FOR CARRYING OUT THE INVENTION

Figure 1:
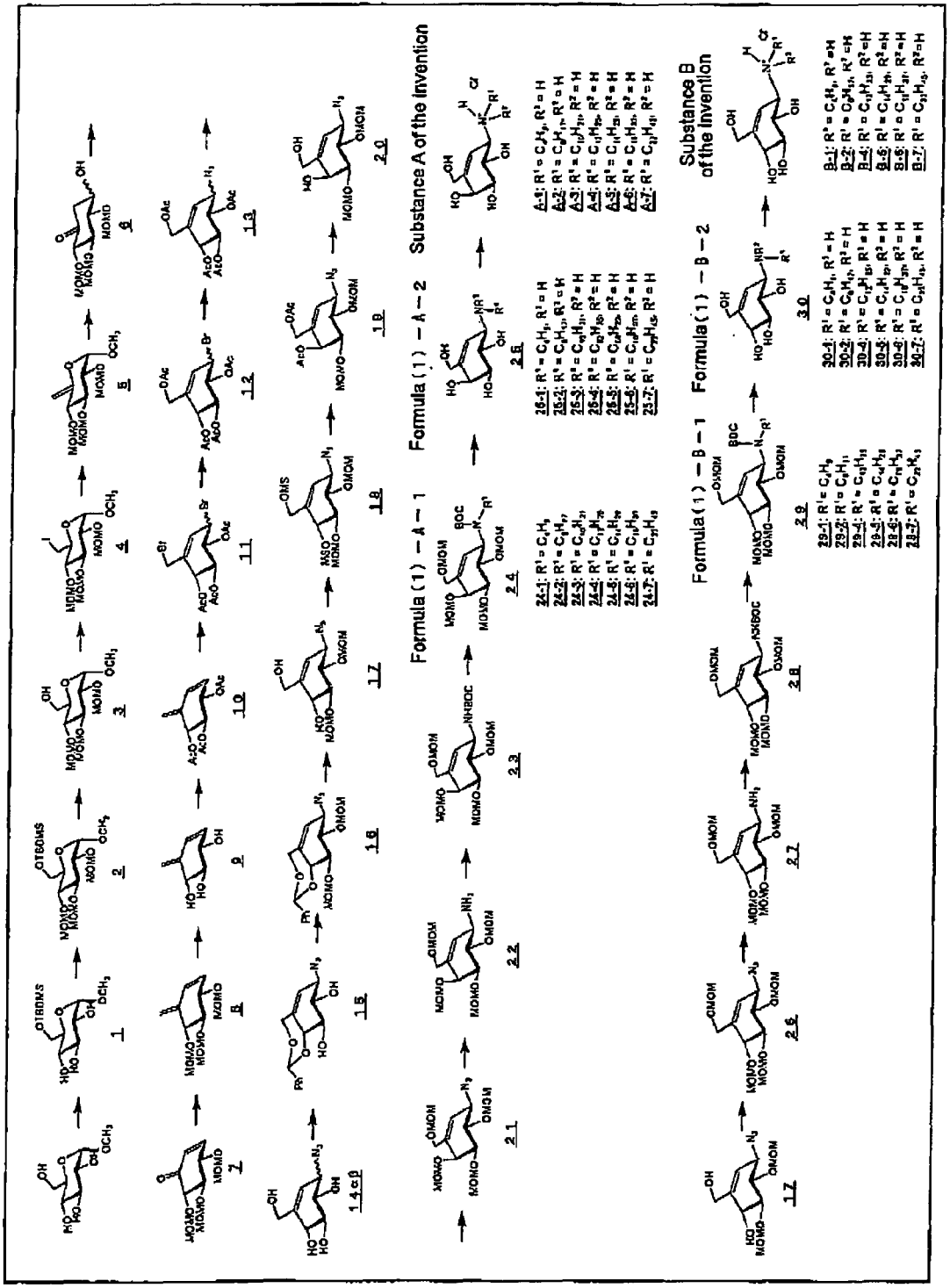
FIG. 1 is a graph showing a scheme for synthesizing the substance of the invention. In the drawing, MOM represents a methoxymethyl group, and BOC represents a t-butoxycarbonyl group, Ac represents a acetyl group, Ph represents a phenyl group, and MS represents methanesulfonic acid.

The invention is specifically described below based on examples.

<1> Synthesis of Compounds (1) Synthesis of Compound 1

A starting material (methyl-α-D-glucopyranoside, manufactured by Sigma) (10 g, 51.493 mmol) was dissolved in dimethylformamide (150 ml), and imidazole (3.856 g, 56.642 mmol) was added thereto. Then, the mixture was cooled to 0° C., and t-butyldimethylsilyl chloride (8.536 g, 56.642 mmol) was added thereto, followed by stirring for 1.5 hours in argon atmosphere. After completion of the reaction, the solvent was evaporated to obtain Compound 1 quantitatively.

TLC: Rf=0.46 (chloroform:methanol=4:1)
$^1$H-NMR (500 MHz; CDCl$_3$)
δ=3.778 (dd, 1H), 3.730 (dd, 1R), 3.647 (t, 1H), 3.512-3.481 (m, 1H), 3.438-3.402 (m, 2H), 3.324 (s, 3H)

(2) Synthesis of Compound 2

Compound 1 (51.493 mmol) was dissolved in 1,2-dichloroethane (50 ml), and N-diisopropylethylamine (53.824 ml 308.994 mmol) was added thereto. Then, chloromethyl methyl ether (14.08 ml, 185.396 mmol) was added dropwise thereto at 60° C. in argon atmosphere, followed by stirring for 1.5 hours. After completion of the reaction, the solvent was evaporated, and the residue was diluted with ethyl acetate and washed with water and saturated brine in this order. The solvent was evaporated, and the residue was purified by silica gel column chromatography (toluene:ethyl acetate=10:0-7:3) to obtain 19.971 g (88%) of Compound 2.

TLC: Rf=0.43 (toluene:ethyl acetate=1:1)
δ=4.822-4.682 (m, 7H), 3.882 (t, 1H), 3.854 (dd, 1H), 3.751 (dd, 1H), 3.582-3.549 (m, 1H), 3.480-3.433 (m, 2H), 3.396 (s, 3H), 3.391 (s, 3H), 3.380 (s, 3H), 3.376 (s, 3H)

(3) Synthesis of Compound 3

Compound 2 (19.971 g, 45.327 mmol) was dissolved in tetrahydrofuran (THF) (30 ml), and 1 M tetrabutylammonium fluoride/tetrahydrofuran (58.925 ml, 58.925 mmol) was added dropwise thereto, followed by stirring at room temperature for 40 minutes in argon atmosphere. After completion of the reaction, the solvent was evaporated, and the residue was diluted with ethyl acetate and washed with water and saturated brine in this order. The solvent was evaporated, and the residue was purified by silica gel column chromatography (toluene:ethyl acetate=1:1-3:7) to obtain 13.298 g (90%) of Compound 3.

TLC: Rf=0.45 (toluene:ethyl acetate=2:1)
$^1$H-NMR (500 MHz, CDCl$_3$)
δ=4.930 (d, 1H, J$_{gem}$=6.4, CH$_3$OC$\underline{H}_2$—), 4.843 (d, 1H, J$_{gem}$=6.4, CH$_3$OC$\underline{H}_2$—), 4.833 (d, 1H, J$_{1-2}$=3.4, H-1), 4.782 (d, 1H, J$_{gem}$=6.4, CH$_3$OC$\underline{H}_2$—), 4.774 (d, 1H, J$_{gem}$=6.8, CH$_3$OC$\underline{H}_2$—), 4.714 (d, 1H, J$_{gem}$=6.8, CH$_3$OC$\underline{H}_2$—), 4.706 (d, 1H, J$_{gem}$=6.4, CH$_3$OC$\underline{H}_2$—), 3.942 (t, 1H, J=9.3, H-4 or 3), 3.897 (ddd, 1H, J$_{6B-5}$=3.5, J$_{6B-OH}$=6.1, J$_{gem}$=12.6, H-6B), 3.789 (ddd, 1H, J$_{6A-5}$=2.2, J$_{6A-OH}$=8.3, J$_{gem}$=12.7, H-6A), 3.640 (ddd, 1H, J$_{5-6A}$=2.2, J$_{5-6B}$=3.3, J$_{5-4}$=10.1, H-5), 3.581 (dd, 1H, J=8.9, J=9.9, H-3 or 4), 3.524 (dd, 1H, J$_{2-1}$=3.8, J$_{2-3}$=9.6, H-2), 3.446, 3.415, 3.412, 3.400 (s, 3H, C$\underline{H}_3$OCH$_2$—)×4, 2.646 (dd, 1H, J$_{OH-6A}$=8.2, J$_{OH-6A}$=6.2, OH)

(4) Synthesis of Compound 4

Compound 3 (13.298 g, 40.746 mmol) was dissolved in pyridine (45 ml), and triphenylphosphine (17.101 g, 65.198 mmol) was added thereto. Then, N-iodosuccinimide (14.608 ml, 65.198 mmol) was gradually added thereto, followed by stirring at room temperature for 4 hours in argon atmosphere. After completion of the reaction, the reaction was stopped by adding methanol (30 ml), and the solvent was evaporated. The residue was diluted with ethyl acetate and washed with saturated sodium bicarbonate water and saturated brine in this order. The solvent was evaporated, and the residue was purified by silica gel column chromatography (toluene:ethyl acetate=7:3) to obtain 14.650 g (82%) of Compound 4.

TLC: Rf=0.37 (toluene:ethyl acetate=3:1)
$^1$H-NMR (500 MHz, CDCl$_3$)
δ=4.922 (d, 1H, J$_{gem}$=6.6, CH$_3$OC$\underline{H}_2$—), 4.842 (d, 1H, J$_{1-2}$=3.7, H-1), 4.824 (d, 1H, J$_{gem}$=6.1, CH$_3$OC$\underline{H}_2$—), 4.776 (d, 1H, J$_{gem}$=6.8, CH$_3$OC$\underline{H}_2$—), 4.775 (d, 1H, J$_{gem}$=5.9, CH$_3$OC$\underline{H}_2$—), 4.742 (d, 1H, J$_{gem}$=6.6, CH$_3$OC$\underline{H}_2$—), 4.710 (d, 1H, J$_{gem}$=6.8, CH$_3$OC$\underline{H}_2$—), 3.930 (dd, 1H, J=9.0, J=9.8, H-3), 3.621 (dd, 1H, J$_{6B-5}$=2.6, J$_{gem}$=10.6, H-6B), 3.516 (dd, 1H, J$_{2-1}$=3.5, J$_{2-3}$=9.9, H-2), 3.506 (m, 1H, H-5), 3.485, 3.428, 3.407, 3.398 (s, 3H, C$\underline{H}_3$OCH$_2$—)×4, 3.311-3.355 (dd×2, 2H, H-4, H-6A)

(5) Synthesis of Compound 5

Compound 4 (3.998 g, 9.165 mmol) was dissolved in toluene (12 ml), and DBU (6.853 ml, 45.825 mmol) was added thereto, followed by stirring at 50° C. for 17 hours in argon atmosphere. After completion of the reaction, the solvent was evaporated, and the residue was purified by silica gel column chromatography (toluene; ethyl acetate=7.3) to obtain 1.638 g (58%) of Compound 5.

TLC: Rf=0.54 (toluene:methanol=20:1)
$^1$H-NMR (500 MHz, CDCl$_3$)
δ=4.885 (d, 1H, J$_{1-2}$=3.4, H-1), 4.840 (m, 5H), 4.780 (d, 1H, J=6.6), 4.734 (d×2, 2H), 4.030 (dt, 1H, J=2.0, J=9.3), 3.930 (t, 1H, J=9.40), 3.649 (dd, 1H, J=3.4, 9.6, H-2), 3.469, 3.466, 3.427, 3.413 (s, 3H, C$\underline{H}_3$O—)×4

(6) Synthesis of Compound 7

Compound 5 (180.8 mg, 0.5864 mmol) was dissolved in a mixed solution of dioxane (6 ml) and water (4 ml), and palladium chloride (13.8 mg, 0.07782 mmol) was added thereto, followed by stirring at 60° C. for 4 hours. After completion of the reaction, the reaction solution was concentrated, diluted with 50 ml of saturated brine and extracted 5 times with 50 ml of ethyl acetate. The resulting organic layer was dried over magnesium sulfate, and the solvent was evaporated under reduced pressure to obtain Compound 6 (141 mg). Compound 6 was dissolved in pyridine (3 ml), and acetic anhydride (3 ml) was added thereto, followed by stirring at 60° C. for 3.5 hours. After completion of the reaction, the solvent was evaporated, and the residue was purified by silica gel column chromatography (toluene:ethyl acetate=4:1, 0.2% triethylamine) to obtain 127.4 mg (78.6%) of Compound 7.

TLC: Rf=0.42 (toluene:ethyl acetate=2:1)
$^1$H-NMR (500 MHz, CDCl$_3$)
δ=6.880 (dd, 1H, J=2.1, J=10.4), 6.055 (dd, 1H, J=2.4, J=10.5), 4.942 (d, 1H, J=6.8, CH$_3$OC$\underline{H}_2$—), 4.929 (d, 1H, J=6.8, CH$_3$OC$\underline{H}_2$—), 4.903 (d, 1H, J=6.3, CH$_3$OC$\underline{H}_2$—), 4.854 (d, 1H, J=6.8, CH$_3$OC$\underline{H}_2$—), 4.838 (d, 1H, J=6.6, CH$_3$OC$\underline{H}_2$—), 4.816 (d, 1H, J=6.8, CH$_3$OC$\underline{H}_2$—), 4.457 (dt, 1H, J=2.2, J=8.3), 4.229 (d, 1H, J=11.0), 3.993 (dd, 1H, J=8.3, J=11.0), 3.489, 3.469, 3.443 (s, 3H, C$\underline{H}_3$OCH$_2$—)×3

(7) Synthesis of Compound 8

Compound 7 (127.4 mg, 0.4132 mmol) was dissolved in anhydrous tetrahydrofuran (10 ml), and 0.5 M Tebbe Reagent/toluene (1.65 ml, 0.825 mmol) was added thereto, followed by stirring for 1.5 hours under ice-cooling. The reaction solution was diluted with ethyl acetate and washed with saturated sodium bicarbonate water and saturated brine in this order. The solvent was evaporated under reduced pressure, and the resulting residue was purified by silica gel column chromatography (toluene:ethyl acetate=6:1, 0.2% triethylamine) to obtain 54.5 mg of Compound 8 (37.5% from Compound 5 by 3 steps).

TLC: Rf=0.53 (toluene:ethyl acetate=2:1)

$^1$H-NMR (500 MHz, CDCl$_3$)

δ=6.186 (dd, 1H, J=1.8, J=10.1), 5.723 (br.d, 1H, J=10.0), 5.290 (br.s, 1H), 5.123 (br.s, 1H), 4.919 (d, 1H, J=6.6), 4.847 (m, 3H), 4.795 (d, 1H, J=6.6), 4.769 (d, 1H, J=6.8), 4.263 (m, 2H), 3.782 (dd, 1H, J=7.0, J=9.4), 3.464, 3.435, 3.429 (s, 3H, CH$_3$OCH$_2$—)×3

(8) Synthesis of Compound 10

Compound 8 (38.4 mg, 0.140 mmol) was dissolved in methanol (3 ml), and trifluoroacetic acid (1.5 ml) was added thereto, followed by stirring under heating at 70° C. for 5 hours. Trifluoroacetic acid (0.5 ml×3) was further added thereto, followed by stirring for 4.5 hours. After completion of the reaction, the solvent was evaporated under reduced pressure to obtain Compound 9. Then, the resulting Compound 9 was dissolved in pyridine (1.5 ml), and acetic anhydride (1.5 ml) was added thereto, followed by stirring at room temperature for 1.5 hours. After completion of the reaction, the solvent was evaporated under reduced pressure, and the resulting residue was purified by silica gel column chromatography (toluene:ethyl acetate=5:1) to obtain 29.4 mg (75%) of Compound 10.

TLC: Rf=0.50 (toluene:ethyl acetate=3:1)

$^1$H-NMR (500 MHz, CDCl$_3$)

δ=6.280 (m, 1H), 5.703 (m, 1H), 5.628 (m, 2H), 5.293 (dd, 1H, J=7.8, J=10.5), 5.187 (m, 1H), 5.055 (m, 1H), 2.141, 2.068, 2.052 (s, 3H, CH$_3$C=O)×3

(9) Synthesis of Compound 11

In argon atmosphere, a carbon tetrachloride solution (1,670 ml) of Compound 10 (20.11 g, 75.0 mmol) was stirred, and bromine (0.3128 mmol/ml carbon tetrachloride solution, 237.3 ml, 74.3 mmol) was added dropwise thereto over 6 hours. After further stirring 30 minutes, the reaction solution was diluted with carbon tetrachloride and washed with saturated sodium bicarbonate water and water in this order. After drying the resulting organic layer over magnesium sulfate, the solvent was evaporated under reduced pressure, and the resulting residue was purified by silica gel column chromatography (toluene ethyl acetate=20:1) to obtain Compound 11 (30.11 g, 94%).

TLC: Rf=0.47, 0.52 (toluene:ethyl acetate=4:1)

Compound 11α

$^1$H-NMR (500 MHz, CDCl$_3$)

δ=6.196 (d, 1H, J=5.6), 6.016 (d, 1H, J=7.8), 5.655 (dd, 1H, J=7.8, J=10.7), 4.948 (m, 2H), 4.001 (d, 1H, J=10.7), 3.855 (d, 1H, J=10.7), 2.131, 2.110, 2.065 (s, 3H, CH$_3$C=O)×3

Compound 11β

$^1$H-NMR (500 MHz, CDCl$_3$)

δ=6.125 (br.s, 1H), 5.962 (m, 1H), 5.532 (dd, 1H, J=8.3, J=10.5), 5.228 (dd, 1H, J=7.8, J=10.5), 4.671 (m, 1H), 4.016 (m, 1H), 3.834 (dd, 1H, J=0.5, J=10.7), 2.101, 2.088, 2.031 (s, 3CH$_3$C=O)×3

(10) Synthesis of Compound 13

Potassium acetate (3.97 g, 40.5 mmol) was added to a dimethylformamide solution (DMF) (2,610 ml) of Compound 11 (19.85 g, 46.4 mmol), followed by stirring for 2 hours, potassium acetate (579 mg, 5.90 mmol) was further added thereto, followed by stirring for 2 hours, and sodium azide (6.05 g, 93.1 mmol) was further added thereto, followed by stirring for 4 hours. The solvent of the reaction solution was evaporated under reduced pressure, and the resulting residue was diluted with ethyl acetate and washed with water and saturated brine in this order. After drying the resulting organic layer with magnesium sulfate, the solvent was evaporated under reduced pressure, and the residue was purified by silica gel column chromatography (toluene:ethyl acetate=10:1) to obtain Compound 13 (8.74 g, 48%).

Compound 13αβ

TLC; Rf=0.23, 0.30 (toluene:ethyl acetate=5:1)

$^1$H-NMR (500 MHz, CDCl$_3$)

δ=5.929 (m, 1H, β), 5.771 (m, 2H, α), 5.659 (m, 1H, β), 5.499 (dd, 1H, J=7.2, J=10.6, β), 5.292 (m, 2H, α), 5.177 (dd, 1H, J=4.4, J=10.5, β), 4.693 (m, 1H, α, 1H, β), 4.410 (m, 1H, α, 2H, β), 4.244 (m, 1H, α), 2.105, 2.071, 2.046, 2.028 (s, 3H, CH$_3$C=O, α)×4, 2.128, 2.064, 2.046 (s, 3H, CH$_3$C=O, β)×4

(11) Synthesis of Compound 14

In argon atmosphere, sodium methoxide (1.26 g, 23.3 mmol) was added to a methanol solution (1,000 ml) of Compound 13 (85.83 g, 232.4 mmol), followed by stirring at room temperature for 90 minutes. The reaction solution was neutralized with Amberlist 15 DRY (trade name, manufactured by Organo Corporation) and filtered through Celite. The filtrate was combined with the resin after washing (tetrahydrofuran:MeOH=1:1), the solvent was evaporated under reduced pressure, and the resulting residue was purified by silica gel column chromatography (chloroform:methanol=5:1) to obtain Compound 14αβ (37.48 g, 93%).

TLC: Rf=0.24 (chloroform:methanol=5:1)

$^1$H-NMR (500 MHz, CD$_3$OD)

δ=5.771 (m, 0.4H), 5.526 (m, 1H), 4.154 (m, 2.8H), 4.093 (m, 1H), 3.970 (m, 1.4H), 3.680 (m, 0.4H), 3.464 (m, 2H), 3.306 (m, 1H)

(12) Synthesis of Compound 15

In argon atmosphere, benzaldehyde dimethyl acetal (36.3 ml, 0.242 mmol) and p-toluenesulfonic acid (3.54 g, 18.6 mmol) were added to a dimethylformamide solution (700 ml) of Compound 14 (37.48 g, 186 mmol), followed by stirring at room temperature for 1.5 hours and then at 45° C. for 3.5 hours. p-Toluenesulfonic acid (1.06 g, 5.57 mmol) was further added thereto, followed by stirring for 3.5 hours. About 7 ml of the solvent in the reaction solution was evaporated under reduced pressure, and the residue was stirred at 45° C. for 1 hour. The reaction solution was ice-cooled and stirred by adding triethyl amine (34.0 ml, 0.244 mmol), and the solvent was evaporated under reduced pressure. The resulting residue was purified by silica gel column chromatography (toluene:ethyl acetate=2:1, 0.5% triethylamine) and further recrystallized from dichloromethane and diisopropyl ether to obtain Compound 15 (26.01 g, 72%).

TLC: Rf=0.44 (toluene:ethyl acetate=1:1)

$^1$H-NMR (500 MHz, CDCl$_3$)

δ=7.483 (m, 2H, Ph), 7.382 (m, 3H, Ph), 5.663 (s, 1H, CH-Ph), 5.471 (br.s, 1H, H-5a), 4.495 (m, 2H, H-6A, H-6B), 4.451 (m, 1H, H-4), 4.184 (m, 1H, H-1), 3.894 (dq, 1H, J=2.9, J=10.5, J=2.7, J=10.5, H-3), 3.730 (dq, 1H, J=2.2, J=10.5, J=2.2, J=10.5, H-2), 2.887 (d, 1H, J=2.2, OH), 2.850 (d, 1H, J=2.9, OH)

(13) Synthesis of Compound 16

In argon atmosphere, N-ethyldiisopropylamine (173 ml, 993 mmol) was added to a dichloroethane solution (450 ml) of Compound 15 (14.36 g, 49.6 mmol), and chloromethyl methyl ether (37.7 ml, 496 mmol) was added dropwise thereto, followed by stirring at room temperature for 15 minutes and then at 60° C. for 6.5 hours. The reaction solution was ice-cooled, triethylamine (138 ml, 993 mmol) was added thereto, and ethanol (77.7 ml, 1.34 mol) was added dropwise thereto, followed by stirring at room temperature for 35 minutes. The solvent in the reaction solution was evaporated under reduced pressure, the resulting residue was dissolved in ethyl acetate and washed with saturated sodium bicarbonate water and saturated brine in this order, the resulting organic layer was dried over magnesium sulfate, and the solvent was evaporated under reduced pressure. The resulting residue was purified by silica gel column chromatography (toluene:ethyl acetate=20:1, 0.5% triethylamine) to obtain Compound 16 (18.18 g, 97%).

TLC: Rf=0.52 (toluene:ethyl acetate=4:1)

$^1$H-NMR (500 MHz, CDCl$_3$)

δ=7.469 (m, 2H, Ph), 7.355 (m, 3H, Ph), 5.650 (s, 1H, C$\underline{H}$-Ph), 5.503 (br.s, 1H, H-5a), 4.989 (d, 1H, J=6.6, CH$_3$OC$\underline{H}_2$—), 4.892 (d, 1H, J=6.4, CH$_3$OC$\underline{H}_2$—), 4.838 (d, 1H, J=6.4, CH$_3$OC$\underline{H}_2$—), 4.817 (d, 1H, J=6.4, CH$_3$OC$\underline{H}_2$—), 4.528 (m, 1H), 4.472 (m, 2H), 4.079 (m, 1H), 3.980 (dd, 1H, J=7.7, J=10.6), 3.674 (dd, 1H, J=8.7, J=10.6), 3.508, 3.363 (s, 3H, C$\underline{H}_3$OCH$_2$—)×2

(14) Synthesis of Compound 17 p-Toluene sulfonic acid (3.53 g, 18.6 mmol) was added to a methanol solution (210 ml) of Compound 16 (14.0 g, 37.1 mmol), followed by stirring at room temperature for 20 minutes. The reaction solution was ice-cooled, triethylamine (25.8 ml, 185 mmol) was added thereto, and the solvent was evaporated under reduced pressure. The resulting residue was purified by silica gel column chromatography (chloroform:methanol=40:1, 0.5% triethylamine) to obtain Compound 17 (8.67 g, 81%).

TLC; Rf=0.39 (chloroform:methanol=20:1)

$^1$H-NMR (500 MHz, CDCl$_3$)

δ=5.598 (br.s, 1H, H-5a), 4.905 (d, 1H, J=6.6, CH$_3$OC$\underline{H}_2$—), 4.826 (d, 1H, J=6.8, CH$_3$OC$\underline{H}_2$—), 4.781 (d, 1H, J=6.8, CH$_3$OC$\underline{H}_2$—), 4.767 (d, 1H, J=6.8, CH$_3$OC$\underline{H}_2$—), 4.569 (d, 1H, J=2.4), 4.294 (m, 1H), 4.259 (br.d, 1H, J=3.7), 4.184 (br.dd, 1H, J=7.2, J=13.1), 4.021 (m, 1H), 3.686 (dd, 1H, J=8.3, J=10.0), 3.531 (dd, 1H, J=7.3, J=10.0), 3.492, 3.480 (s, 3H, C$\underline{H}_3$OCH$_2$—)×2, 2.572 (br.dd, 1H, J=4.6, J=7.8)

(15) Synthesis of Compound 19

Triethylamine (120 ml, 861.0 mmol) and methanesulfonic acid chloride (67 ml, 865.7 mmol) were added to a dichloromethane solution (600 ml) of Compound 17 (12.49 g, 43.2 mmol), followed by stirring at 0° C. for 45 minutes. After completion of the reaction, triethylamine (150 ml) and methanol (300 ml) were added thereto, and the solvent was evaporated under reduced pressure. The residue was dissolved in ethyl acetate and washed with saturated sodium bicarbonate water and saturated brine in this order, the resulting organic layer was dried over magnesium sulfate, and the solvent was evaporated under reduced pressure to obtain Compound 18.

Then, Compound 18 was dissolved in toluene (600 ml), and cesium acetate (24.92 g, 129.8 mmol) and 18-6 crown ether (68.50 g, 259.2 mmol) were added thereto, followed by stirring at 90° C. for 80 minutes. The reaction solution was diluted with ethyl acetate and washed with saturated sodium bicarbonate water and saturated brine in this order, the resulting organic layer was dried over magnesium sulfate, and the solvent was evaporated under reduced pressure. The resulting residue was purified by silica gel column chromatography (toluene:ethyl acetate=4:1, 0.2% triethylamine) to obtain Compound 19 (12.01 g, 74.5%).

TLC: Rf=0.41 (toluene:ethyl acetate=2:1)

$^1$H-NMR (500 MHz, CDCl$_3$)

δ=5.845 (m, 1H), 5.671 (d, 1H, J=3.7), 4.948 (d, 1H, J=6.6, CH$_3$OC$\underline{H}_2$—), 4.770 (d, 1H, J=6.6, CH$_3$OC$\underline{H}_2$—), 4.744 (d, 1H, J=7.1, CH$_3$OC$\underline{H}_2$—), 4.637 (d, 1H, J=6.8, CH$_3$OC$\underline{H}_2$—), 4.525 (m, 2H), 3.936 (m, 2H), 3.834 (dd, 1H, J=3.8, J=9.9), 3.500, 3.397 (s, 3H, C$\underline{H}_3$OCH$_2$—)×2, 2.105, 2.090 (s, 3H, C$\underline{H}_3$C=O)×2

(16) Synthesis of Compound 20

Compound 19 (8.96 g, 24.0 mmol) was dissolved in methanol (300 ml), and sodium methoxide (262.7 mg, 4.863 mmol) was added thereto, followed by stirring at room temperature for 80 minutes. After completion of the reaction, the reaction solution was neutralized with Amberlist 15 DRY (trade name, manufactured by Organo Corporation) and filtered through celite. The solvent was evaporated under reduced pressure, and the resulting residue was purified by silica gel column chromatography (chloroform methanol=40: 1, 0.2% triethylamine) to obtain Compound 20 (5.11 g, 73.6%).

TLC: Rf=0.33 (toluene:acetone=1:1)

$^1$H-NMR (500 MHz, CDCl$_3$)

δ=5.727 (m, 1H, H-5a), 4.889 (d, 1H, J=6.6, CH$_3$OC$\underline{H}_2$—), 4.845 (d, 1H, J=6.8, CH$_3$OC$\underline{H}_2$—), 4.790 (d, 1H, J=6.6, CH$_3$OC$\underline{H}_2$—), 4.786 (d, 1H, J=6.6, CH$_3$OC$\underline{H}_2$—), 4.358 (br.t, J=3.1), 4.245 (br.m, 2H), 3.970 (dd, 1H, J=7.5, J=9.6), 3.874 (m, 1H), 3.700 (dd, 1H, J=3.9, J=9.8), 3.477, 3.444 (s, 3H, C$\underline{H}_3$OCH$_2$—)×2, 3.099 (br, 1H), 2.527 (br, 1H)

(17) Synthesis of Compound 21

In argon atmosphere, N-ethyldiisopropylamine (61.5 ml, 353.06 mmol) was added to a dichloroethane solution (300 ml) of Compound 20 (5.11 g, 17.7 mmol), and chloromethyl methyl ether (13.4 ml, 176.4 mmol) was added dropwise thereto, followed by stirring at room temperature for 15 minutes and then at 60° C. for 5.5 hours. The reaction solution was ice-cooled, triethylamine (60 ml) was added thereto, and ethanol (60 ml) was added dropwise thereto, followed by stirring at room temperature for 35 minutes. The solvent in the reaction solution was evaporated under reduced pressure, the resulting residue was dissolved in ethyl acetate and washed with saturated sodium bicarbonate water and saturated brine in this order, the resulting organic layer was dried over magnesium sulfate, and the solvent was evaporated under reduced pressure. The resulting residue was purified by silica gel column chromatography (toluene:ethyl acetate=3:1, 0.2% triethylamine) to obtain Compound 21 (6.65 g, 99.8%).

TLC: Rf=0.44 (toluene ethyl acetate=1:1)

$^1$H-NMR (500 MH, CDCl$_3$)

δ=5.740 (m, 1H, H-5a), 4.926 (d, 1H, J=6.4, CH$_3$OC$\underline{H}_2$—), 4.874 (d, 1H, J=6.8, CH$_3$OC$\underline{H}_2$), 4.776 (m, 3H, CH$_3$OC$\underline{H}_2$—×3), 4.684 (d, 1H, J=7.1, CH$_3$OC$\underline{H}_2$—) 4.651 (d, 2H, J=6.6, CH$_3$OC$\underline{H}_2$—×2), 4.218 (d, 1H, J=3.2, H-4), 4.118 (m, 2H, 4.079 (dd, 1H, J=7.7, J=10.1, H-2), 3.846 (br.d, 1H), 3.721 (dd, 1H, J=3.3, J=10.1, H-3), 3.485, 3.422, 3.398, 3.385 (s, 3H, C$\underline{H}_3$OCH$_2$—)×4

(18) Synthesis of Compound 22

Water (2.5 ml) and triphenylphosphine (404.1 mg, 1.54 mmol) were added to a toluene solution (10 ml) of Compound 21 (290.4 mg, 0.769 mmol), followed by stirring at 105° C. for 105 minutes. Toluene and ethanol were added to the reaction solution, evaporation of the solvent under reduced pressure was repeated 3 times, and the resulting residue was purified by silica gel column chromatography (chloroform:methanol=20:1, 0.5% triethylamine) to obtain Compound 22 (267.3 mg, 99%).

TLC: Rf=0.47 (chloroform:methanol=10:1)

$^1$H-NMR (500 MHz, CDCl$_3$)

δ=5.754 (m, 1H), 4.903 (d, 1H, J=6.8, CH$_3$OCH$_2$—), 4.898 (d, 1H, J=6.6, CH$_3$OCH$_2$—), 4.767 (m, 3H, CH$_3$OCH$_2$—×3), 4.695 (d, 1H, J=6.8, CH$_3$OCH$_2$—), 4.658 (d, 1H, J=6.6, CH$_3$OCH$_2$—), 4.638 (d, 1H, J=6.6, CH$_3$OCH$_2$—), 4.252 (d, 1H, J=2.7, H-4), 4.124 (dt, 1H, J=1.7, J=12.2), 4.039 (dtm, 1H, J=1.0, J=12.2), 3.704 (m, 2H), 3.455, 3.420, 3.410, 3.385 (s, 3H, CH$_3$OCH$_2$—)×4

(19) Synthesis of Compound 23

In argon atmosphere, triethylamine (4.13 ml, 29.6 mmol) was added to a dichloromethane solution (50 ml) of Compound 22 (2.60 g, 7.40 mmol), followed by ice-cooling, and di-t-butyl dicarbonate (3.40 ml, 14.8 mmol) was added thereto, followed by stirring for 80 minutes while gradually raising the temperature of the reaction solution to room temperature. The reaction solution was ice-cooled, diluted with ethyl acetate and washed with saturated sodium bicarbonate water and saturated brine in this order, the resulting organic layer was dried over magnesium sulfate, and the solvent was evaporated under reduced pressure. The resulting residue was purified by silica gel column chromatography (toluene:ethyl acetate=3:2, 0.5% triethylamine) to obtain Compound 23 (3.31 g, 99%).

TLC: Rf=0.25 (toluene:ethyl acetate=1:1)

$^1$H-NMR (500 MHz, CDCl$_3$)

δ=5.752 (br.s, 1H), 4.911 (br.d, 1H, J=8.6), 4.862 (d, 1H, J=6.8, CH$_3$OCH$_2$—), 4.833 (d, 1H, J=6.8, CH$_3$OCH$_2$—), 4.780 (d, 1H, J=6.6, CH$_3$OCH$_2$—), 4.749 (d, 1H, J=6.6, CH$_3$OCH$_2$—), 4.693 (d, 1H, J=6.8, CH$_3$OCH$_2$—), 4.690 (d, 1H, J=6.8, CH$_3$OCH$_2$—), 4.645 (d, 1H, J=6.6, CH$_3$OCH$_2$—), 4.623 (d, 1H, J=6.6, CH$_3$OCH$_2$—), 4.295 (d, 1H, J=2.0, H-4), 4.241 (br, 1H), 4.119 (br.d, 1H, J=12.7), 4.035 (br.d, 1H, J=12.5), 3.854 (m, 2H), 3.413, 3.405, 3.400, 3.371 (s, 3H, CH$_3$OCH$_2$—)×4

(20) Synthesis of Compound 24-1

In argon atmosphere, a DMP solution (1.5 ml) of Compound 23 (100 mg, 0.221 mmol) was ice-cooled, and sodium hydride (60% in oil, 31.8 mg, 0.795 mmol) was added thereto, followed by stirring for 10 minutes under ice-cooling, Then, bromobutane (31.6 µl, 0.831 mmol) was added thereto, followed by stirring for 4 hours while gradually raising the temperature of the reaction solution to room temperature. The reaction solution was ice-cooled, and methanol (1 ml) was added dropwise thereto, followed by stirring for 30 minutes. The reaction solution was diluted with ethyl acetate and stirred by adding saturated sodium bicarbonate water, the organic layer was washed with saturated sodium bicarbonate water and saturated brine in this order and dried over magnesium sulfate, and the solvent was evaporated under reduced pressure. The resulting residue was purified by silica gel column chromatography (toluene:ethyl acetate 2:1, 0.2% triethylamine) to obtain Compound 24-1 (102.3 mg, 91.0%). Developing solvent of Compound 241 (toluene; ethyl acetate=2:1) Rf: 0.32

C$_{24}$H$_{45}$NO$_{10}$ MW: 507.61

$^1$H-NMR (500 MHz, CDCl$_3$)

δ=5.574 (br.d, 1H, H-5a), 4.910, 4.871 (2d, 2H, J=6.8 Hz, 6.8 Hz, OCH$_2$), 4.801-4.618 (m, 6H, 3OCH$_2$), 4.188 (br.d, 1H), 4.112-4.039 (m, 3H), 3.737 (br.d, 1H), 3.406, 3.387, 3.368, 3.348 (4s, 12H, 4OCH$_3$), 3.135 (m, 1H, NCH$_2$), 2.907 (m, 1H, NCH$_2$), 1.66-1.22 (m, 4H, 2CH$_2$), 1.464 (s, 9H, CC(CH$_3$)$_3$), 0.892 (t, 3H, J=7.3 Hz, CH$_3$)

(21) Synthesis of Compound 25-1

Hydrochloric acid (4 N, 6.5 ml) was added to a THF solution (4.0 ml) of Compound 24-1 (102 mg, 0.201 mmol), followed by stirring at 45° C. for 5 hours. The solvent of the reaction solution was evaporated under reduced pressure, and the resulting residue was azeotroped with ethanol 3 times. The resulting residue was purified by Sephadex LH-20 (trade name, manufactured by Pharmacia Biotech) (chloroform:methanol=1:2). Then, the mixture was dissolved in water (1 ml), 25% aqueous ammonia (1 ml) was added thereto, and the reaction solution was directly purified by silica gel column chromatography (chloroform:methanol:water=60:35:8) to obtain Compound 25-1 (15 mg, 32.3%).

Developing solvent of Compound 25-1 (chloroform:methanol:water=60:35:8) Rf: 0.15

C$_{11}$H$_{21}$NO$_4$ MW: 231.29

$^1$H-NMR (500 MHz, CD$_3$OD)

δ=5.723 (d, 1H, J=2.0 Hz, H-5a), 4.155 (d, 1H, J=4.2 Hz, H-4), 4.128 (br.s, 2H, H-6), 3.726 (dd, 1H, J=8.3 Hz, 10.0 Hz, H-2), 3.447 (dd, 1H, J=J=4.2 Hz, 10.1 Hz, H-3), 3.169 (br.d, 1H, H-1), 2.756 (br.ddd, 1H, NCH$_2$), 2.621 (br.ddd, 1H, NCH$_2$), 1.56-1.28 (m, 4H, 2CH$_2$), 0.953 (t, 3H, 3=7.3 Hz, CH$_3$)

(22) Synthesis of Compound 24-2

In argon atmosphere, dimethylformamide solution (50 ml) of Compound 23 (3.31 g, 7.33 mmol) was ice-cooled, and sodium hydride (60% in oil, 1051.0 mg, 26.3 mmol) was added thereto, followed by stirring for 10 minutes under ice-cooling. Then, n-octyl bromide (1.90 ml, 10.99 mmol) was added dropwise thereto, followed by stirring for 140 minutes while gradually raising the temperature of the reaction solution to room temperature. The reaction solution was ice-cooled and methanol (1.78 ml) was added dropwise thereto, followed by stirring for 30 minutes. The reaction solution was diluted with diethyl ether (200 ml) and saturated sodium bicarbonate water (100 ml) was added thereto, followed by stirring. Then, the organic layer was washed with saturated sodium bicarbonate water and saturated brine in this order and dried over magnesium sulfate, and the solvent was evaporated under reduced pressure. The resulting residue was purified by silica gel column chromatography (toluene ethyl acetate=3:1, 0.5% triethylamine) to obtain Compound 24-2 (3.62 g, 88%).

Developing solvent of Compound 24-2 (toluene:ethyl acetate=1:1) Rf: 0.40

$^1$H-NMR (500 MHz, CDCl$_3$)

C$_{28}$H$_{53}$NO$_{10}$ MW: 563.72

δ=5.573 (br.s, 1H), 4.909 (d, 1H, J=6.8, CH$_3$OCH$_2$—), 4.873 (d, 1H, J=6.8, CH$_3$OCH$_2$—), 4.794 (br.d, 1H, J=6.6, CH$_3$OCH$_2$—), 4.740 (d, 1H, J=6.4, CH$_3$OCH$_2$—), 4.699 (d, 1H, J=6.8, CH$_3$OCH$_2$—), 4.633 (m, 3H, CH$_3$OCH$_2$—×3), 4.190 (br.s, 1H), 4.089 (m, 3H), 3.736 (br.d, 1H, J=10.3), 3.406, 3.390, 3.366, 3.345 (s, 3H, CH$_3$OCH$_2$—)×4, 3.121 (br, 1H), 2.894 (br, 1H), 1.462 (br×2, 9H, t-butyl), 1.261 (br.m, 12H, H-2'-7'), 0.878 (t, 3H, H-8')

(23) Synthesis of Compound 25-2

Hydrochloric acid (4 N, 187 ml) was added to a THF solution (123 ml) of Compound 24-2 (3.85 g, 6.83 mmol), followed by stirring at 45° C. for 3 hours. The solvent of the reaction solution was evaporated under reduced pressure, and the resulting residue was azeotroped with 300 ml of ethanol 3 times. The resulting residue was purified by Sephadex LH-20 (trade name, manufactured by Pharmacia Biotech) (chloroform:methanol=1:1). Then, the mixture was dissolved in water (200 ml), and 25% aqueous ammonia (10 ml) was added thereto. Ten minutes thereafter, the precipitated crystals were collected by filtration to obtain Compound 25-2 (1.35 g, 72.1%).

Melting point: 80.9-82.3° C.

$[\alpha]^{20}{}_D$ =+9.83° (c=1.0 methanol)

$^1$H-NMR (500 MHz, 1:2=CD$_3$OD:CDCl$_2$)

δ=5.734 (br.d, 1H, H-5a), 4.268 (br.d, 1H, H-6a), 4.153 (d, 1H, J=4.1 Hz, H-1), 4.133 (br.d, 1H, H-6b), 3.953 (dd, 1H, J=8.1, 9.8 Hz, H-3), 3.638 (br.d, 1H, H-4), 3.549 (dd, 1H, J=4.1, 9.8 Hz, H-2), 3.063 (m, 2H, H-1'×2), 1.75 1.26 (m, 12H, 6CH$_2$, H-2'-7'), 0.894 (t, 3H, J=7.1 Hz, CH$_3$, H-8')

(24) Synthesis of Compound 243

In argon atmosphere, a DMF solution (2 ml) of Compound 23 (85 mg, 0.188 mmol) was ice-cooled, and sodium hydride (60% in oil, 26.7 mg, 0.668 mmol) was added thereto, followed by stirring for 10 minutes under ice-cooling. Then, 1-bromodecane (58.6 µl, 0.283 mmol) was added dropwise thereto, followed by stirring for 3 hours while gradually raising the temperature of the reaction solution to room temperature. The reaction solution was ice-cooled, and ethanol (1 ml) was added dropwise thereto, followed by stirring for 30 minutes. The reaction solution was diluted with ethyl acetate, and saturated sodium bicarbonate water was added thereto, followed by stirring. Then, the organic layer was washed with saturated sodium bicarbonate water and saturated brine in this order and dried over magnesium sulfate, and the solvent was evaporated under reduced pressure. The resulting residue was purified by silica gel column chromatography (toluene:ethyl acetate=4:1, 0.2% triethylamine) to obtain Compound 24-3 (91.5 mg, 82.1%).

Developing solvent of Compound 24-3 (toluene:ethyl acetate=4:1) Rf: 0.27

C$_{30}$H$_{57}$NO$_{10}$ MW: 591.78

$^1$H-NMR (500 MHz, CDCl$_3$)

δ=5.574 (br.d, 1H, H-5a), 4.907, 4.873 (2d, 2H, J=6.6 Hz, 6.7 Hz, OCH$_2$), 4.800-4.617 (m, 6H, 3OCH$_2$), 4.191 (br.d, 1H), 4.113-4.035 (m, 3H), 3.736 (br.d, 1H), 3.406, 3.389 3.366, 3.345 (4s, 12H, 4OCH$_3$), 3.121 (n, 1H, NCH$_2$), 2.895 (m, 1H, NCH$_2$), 1.67-1.25 (m, 16H, 3OCH$_2$), 1.251 (s, 9H, CC(CH$_3$)$_3$), 0.880 (t, 3H, J=7.1 Hz, CH$_3$)

(25) Synthesis of Compound 25-3

Hydrochloric acid (4 N, 6.5 ml) was added to a THF solution (4 ml) of Compound 24-3 (91.5 mg, 0.155 mmol), followed by stirring at 45° C. for 5 hours. The solvent of the reaction solution was evaporated under reduced pressure, and the resulting residue was azeotroped with ethanol 3 times. The resulting residue was purified by Sephadex LH-20 (trade name, manufactured by Pharmacia Biotech) (chloroform:methanol:water=1:2). Then, the mixture was dissolved in water (1 ml), and 25% aqueous ammonia (1 ml) was added thereto. Ten minutes thereafter, the precipitated crystals were collected by filtration to obtain Compound 25-3 (41 mg, 83.9%).

Developing solvent of Compound 25-3 (chloroform:methanol:water=60:35:8) Rf: 0.31

C$_{17}$H$_{33}$NO$_4$ MW: 315.45

$^1$H-NMR (500 MHz, CD$_3$OD)

δ=5.727 (d, 1H, J=2.2 Hz, H-5a), 4.167 (d, 1H, J=4.2 Hz, H-4), 4.143 (br.s, 2H, H-6), 3.684 (dd, 1H, J=8.3 Hz, 10.0 Hz, H-2), 3.463 (dd, 1H, J=4.2 Hz, 10.3 Hz, H-3), 3.124 (br.d, 1H, H-1), 2.762 (br.ddd, 1H, NCH$_2$), 2.571 (br.ddd, 1H, NCH$_2$), 1.55-1.29 (m, 16H, 8CH$_2$), 0.893 (t, 3H, J=7.0 Hz, CH$_3$)

(26) Synthesis of Compound 24-4

In argon atmosphere, a DMF solution (2 ml) of Compound 23 (84 mg, 0.1860 mmol) was ice-cooled, and sodium hydride (60% in oil, 26.7 mg, 0.925 mmol) was added thereto, followed by stirring for 10 minutes under ice-cooling. Lauryl bromide (47.8 µl, 0.279 mmol) was added dropwise thereto, followed by stirring for 3.5 hours while gradually raising the temperature of the reaction solution to room temperature. The reaction solution was ice-cooled, and methanol (1 ml) was added dropwise thereto, followed by stirring for 30 minutes. The reaction solution was diluted with ethyl acetate, and saturated sodium bicarbonate water was added thereto, followed by stirring. Then, the organic layer was washed with saturated sodium bicarbonate water and saturated brine in this order and dried over magnesium sulfate, and the solvent was evaporated under reduced pressure. The resulting residue was purified by silica gel column chromatography (toluene:ethyl acetate=3:1, 0.2% triethylamine) to obtain Compound 24-4 (86.9 mg, 75.4%).

Developing solvent of Compound 24-4 (toluene:ethyl acetate=2:1) Rf: 0.33

C$_{32}$H$_{61}$NO$_{10}$ MW: 619.83

$^1$H-NMR (500 MHz, CDCl$_3$)

δ=5.573 (br.d, 1H H-5a), 4.909, 4.873 (2d, 2H, J=6.8 Hz, 6.7 Hz, OCH$_2$), 4.801-4.616 (m, 6H, 3OCH$_2$), 4.190 (br.d, 1H), 4.112-4.035 (m, 3H), 3.736 (br.d, 1H), 3.406, 3.389, 3.365, 3.345 (4s, 12H, 4OCH$_3$), 3.121 (m, 1H, NCH$_2$), 2.891 (m, 1H, NCH$_2$), 1.65-1.25 (m, 20H, 10CH$_2$), 1.250 (s, 9H, CC(CH$_3$)$_3$), 0.881 (t, 3H, J=7.1 Hz, CH$_3$)

(27) Synthesis of Compound 25-4

Hydrochloric acid (4 N, 4.6 ml) was added to a THF solution (3 ml) of Compound 24-4 (86.9 mg, 0.140 mmol), followed by stirring at 45° C. for 5 hours. The solvent of the reaction solution was evaporated under reduced pressure, and the resulting residue was azeotroped with ethanol 3 times. The resulting residue was purified by Sephadex LH-20 (trade name, manufacured by Pharmacia Biotech) (chloroform:methanol=1:2). Then, the mixture was dissolved in water (1 ml), and 25% aqueous ammonia (1 ml) was added thereto. Ten minutes thereafter, the precipitated crystals were collected by filtration to obtain Compound 25-4 (41.1 mg, 85.5%).

Developing solvent of Compound 25-4 (chloroform:methanol:water=60:35:8) Rf: 0.31

C$_{19}$H$_{37}$NO$_4$ MW: 343.50

$^1$H-NMR (500, MHz, CD$_3$OD)

δ=5.726 (d, 1H, J=2.2 Hz, H-5a), 4.165 (d, 1H, J=4.4 Hz, H-4), 4.138 (br.s, 2H, H-6), 3.682 (dd, 1H, J=8.1 Hz, 10.3 Hz, H-2), 3.457 (dd, 1H, J=4.2 Hz, 10.3 Hz, H-3), 3.110 (br.d, 1H, H-1), 2.752 (br.ddd, 1H, NCH$_2$), 2.558 (br.ddd, 1H, NCH$_2$), 1.55-1.28 (m, 20H, 10CH$_2$), 0.893 (t, 3H, J=7.1 Hz, CH$_3$)

(28) Synthesis of Compound 24-5

In argon atmosphere, a DMF solution (1.5 ml) of Compound 23 (70 mg, 0.155 mmol) was ice-cooled, sodium hydride (60% in oil, 22.2 mg, 0.555 mmol) was added thereto, followed by stirring for 10 minutes under ice-cooling, and myristyl bromide (63 µl, 0.233 mmol) was added dropwise thereto, followed by stirring for 2.5 hours while gradually raising the temperature of the reaction solution to room temperature. The reaction solution was ice-cooled, and methanol (1 ml) was added dropwise thereto, followed by stirring for 30 minutes. The reaction solution was diluted with ethyl acetate, and saturated sodium bicarbonate water was added thereto, followed by stirring. Then, the organic layer was washed with saturated sodium bicarbonate water and saturated brine in this order and dried over magnesium sulfate, and the solvent was evaporated under reduced pressure. The resulting residue was purified by silica gel column chromatography (toluene:ethyl acetate=3:1, 0.2% triethylamine) to obtain Compound 24-5 (85.6 mg, 85.2%).

Developing solvent of Compound 24-5 (toluene: ethyl acetate=3:1) Rf: 0.34

$C_{34}H_{65}NO_{10}$ MW: 647.88

$^1$H-NMR (500 MHz, CDCl$_3$)

δ=5.571 (br.d, 1H, H-5a), 4.907, 4.873 (2d, 2H, J=6.6 Hz, 6.8 Hz, OCH$_2$), 4.800-4.616 (m) 6H, 3OCH$_2$), 4.189 (br.d, 1H), 4.112-4.034 (m, 3H), 3.735 (br.d, 1H), 3.405, 3.388, 3.364, 3.344 (4s, 12H, 4OCH$_3$), 3.119 (m, 1H, NCH$_2$), 2.892 (m, 1H, NCH$_2$), 1.67-1.25 (m, 24H, 12CH$_2$), 1.251 (s, 9H, CC(CH$_3$)$_3$), 0.880 (t 3H, J=7.1 Hz, CH$_3$)

(29) Synthesis of Compound 25-5

Hydrochloric acid (4 N, 4 ml) was added to a THF solution (3 ml) of Compound 24-5 (85.6 mg, 0.132 mmol), followed by stirring at 45° C. for 5 hours. The solvent of the reaction solution was evaporated under reduced pressure, and the resulting residue was azeotroped with ethanol 3 times. The resulting residue was purified by Sephadex LH-20 (trade name, manufactured by Pharmacia Biotech) (chloroform methanol=1:2). Then, the mixture was dissolved in water (1 ml), and 25% aqueous ammonia (1 ml) was added thereto, Ten minutes thereafter, the precipitated crystals were collected by filtration to obtain Compound 25-5 (48.1 mg, 98-1%).

Developing solvent of Compound 25-5 (chloroform: methanol:water=60:35:8) Rf: 0.38

$C_{21}H_{41}NO_4$ MW: 371.55

$^1$H-NMR (500 MHz, CD$_3$OD)

δ=5.726 (d, 1H, J=2.0 Hz, H-5a), 4.165 (d, 1H, J=4.2 Hz, H-4), 4.138 (br.s, 2H, H-6), 3.683 (dd, 1H, J=8.1 Hz, 10.3 Hz, H-2), 3.457 (dd, 1H, J=4.2 Hz, 10.3 Hz, H-3), 3.110 (br.d, 1H, H-1), 2.752 (br.ddd, 1H, NCH$_2$), 2.559 (br.ddd, 1H, NCH$_2$), 1.56-1.28 (m, 24H, 12CH$_2$), 0.894 (t, 3H, J=7.1 Hz, CH$_3$)

(30) Synthesis of Compound 24-6

In argon atmosphere, a DMF solution (1.5 ml) of Compound 23 (70 mg, 0.155 mmol) was ice-cooled, and sodium hydride (60% in oil, 22.2 mg, 0.555 mmol) was added thereto, followed by stirring for 10 minutes under ice-cooling. Then, 1-bromooctadecane (77.5 mg, 0.232 mmol) was added thereto, followed by stirring for 4 hours while gradually raising tile temperature of the reaction solution to room temperature. The reaction solution was ice-cooled, and methanol (1 ml) was added dropwise thereto, followed by stirring for 30 minutes. The reaction solution was diluted with ethyl acetate, and saturated sodium bicarbonate water was added thereto, followed by stirring. Then, the organic layer was washed with saturated sodium bicarbonate water and saturated brine in this order and dried over magnesium sulfate, and the solvent was evaporated under reduced pressure. The resulting residue was purified by silica gel column chromatography (toluene:ethyl acetate=3:1, 0.2% triethylamine) to obtain Compound 24-6 (57.5 mg, 52.7%).

Developing solvent of Compound 24-6 (toluene: ethyl acetate=2:1) Rf 0.36 $C_{38}H_{73}NO_{10}$ MW: 703.99

$^1$H-NMR (500 MHz, CDCl$_3$)

δ=5.572 (br.d, 1H, H-5a), 4.909, 4.873 (2d, 2H, J=6.8 Hz, 6.8 Hz, OCH$_2$), 4.801-4.616 (m, 6H, 3OCH$_2$), 4.190 (br.d, 1H), 4.113-4.035 (m, 3H), 3.739 (br.d, 1H), 3.406, 3.389, 3.365, 3.345 (4s, 12H, 4OCH$_3$), 3.121 (m, 1H, NCH$_2$), 2.887 (m, 1H, NCH$_2$), 1.67-1.25 (m, 32H, 16CH$_2$), 1.255 (s, 9H, CC(CH$_3$)$_3$), 0.880 (t, 3H, J=7.1 Hz, CH$_3$)

(31) Synthesis of Compound 25-6

Hydrochloric acid (4 N, 2.5 ml) was added to a THF solution (2.0 ml) of Compound 24-6 (57.5 mg, 0.082 mmol), followed by stirring at 45° C. for 5 hours. The solvent of the reaction solution was evaporated under reduced pressure, and the resulting residue was azeotroped with ethanol 3 times. The resulting residue was purified by Sephadex LH-20 (trade name, manufactured by Pharmacia Biotech) (chloroform: methanol=1:2). Then, the mixture was dissolved in water (1 ml), and 25% aqueous ammonia (1 ml) was added thereto. Ten minutes thereafter, the precipitated crystals were collected by filtration to obtain Compound 25-6 (26.9 mg, 76.7%).

Developing solvent of Compound 25-6 (chloroform: methanol:water 60:35:8) Rf: 0.43

$C_{25}H_{49}NO_4$ MW: 427.66

$^1$H-NMR (500 MHz, CD$_3$OD)

δ=5.729 (d, 1H, J=1.8 Hz, H-5a), 4.168 (d, 1H, J=4.0 Hz, H-4), 4.145 (br.s, 2H, H-6), 3.675 (dd, 1H, J=8.3 Hz, 10.3 Hz, H-2), 3.463 (dd, 1H, J=4.1 Hz, 10.3 Hz, H-3), 3.109 (br.d, 1H, H-1), 2.754 (br.ddd, 1H, NCH$_2$), 2.557 (br.ddd, 1H, NCH$_2$), 1.53-1.27 (m, 32H, 16CH$_2$), 0.893 (t, 3H, J=7.0 Hz, CH$_3$)

(32) Synthesis of Compound 24-7

In argon atmosphere, a DMF solution (2.0 ml) of Compound 23 (85 mg, 0.188 mmol) was ice-cooled, and sodium hydride (60% in oil, 27.0 mg, 0.675 mmol) was added thereto, followed by stirring for 10 minutes under ice-cooling. Then, bromodocosane (110 mg, 0.282 mmol) was added thereto, followed by stirring for 2 hours while gradually raising the temperature of the reaction solution to room temperature. The reaction solution was ice-cooled, and methanol (1 ml) was added dropwise thereto, followed by stirring for 30 minutes. The reaction solution was diluted with ethyl acetate, and saturated sodium bicarbonate water was added thereto, followed by stirring. Then, the organic layer was washed with saturated sodium bicarbonate water and saturated brine in this order and dried over magnesium sulfate, and the solvent was evaporated under reduced pressure. The resulting residue was purified by silica gel column chromatography (toluene:ethyl acetate=3:1, 0.2% triethylamine) to obtain Compound 24-7 (70.2 mg, 49.1%).

Developing solvent of Compound 24-7 (toluene:ethyl acetate=2:1) Rf: 0.38

$C_{42}H_{81}NO_{10}$ MW: 760.10

$^1$H-NMR (500 MHz, CDCl$_3$)

δ=5.572 (br.d, 1H, H-5a), 4.909, 4.873 (2d, 2H, J=6.6 Hz, 6.8 Hz, OCH$_2$), 4.801-4.616 (m, 6H 3OCH$_2$), 4.190 (br.d, 1H), 4.112-4.035 (m, 3H), 3.736 (br.d, 1H), 3.406, 3.389, 3.365, 3.345 (4s, 12H, 4OCH$_3$), 3.119 (m, 1H, NCH$_2$), 2.887 (m, 1H, NCH$_2$), 1.67-1.25 (m, 40H, 20CH$_2$), 1.254 (s, 9H, CC(CH$_3$)$_3$), 0.880 (t, 3H, J=7.1 Hz, CH$_3$)

(33) Synthesis of Compound 25-7

Hydrochloric acid (4 N. 3.0 ml) was added to a THF solution (2.0 ml) of Compound 24-7 (70.2 mg, 0.092 mmol), followed by stirring at 45° C. for 5 hours. The solvent of the reaction solution was evaporated under reduced pressure, and the resulting residue was azeotroped with ethanol 3 times. The resulting residue was purified by Sephadex LH-20 (trade name, manufactured by Pharmacia Biotech) (chloroform: methanol=1:2). Then, the mixture was dissolved in water (1 ml), and 25% aqueous ammonia (1 ml) was added thereto. Ten minutes thereafter, the precipitated crystals were collected by filtration to obtain Compound 25-7 (27.1 mg, 60.9%).

Developing solvent of Compound 25-7 (chloroform methanol:water=60:35:8) Rf: 0.48

$C_{29}H_{57}NO_4$ MW: 483.77

$^1$H-NMR (500 MHz, $CD_3OD$)

δ=5.727 (d, 1H, J=1.8 Hz, H-5a), 4.166 (d, 1H) J=4.2 Hz, H-4), 4.140 (br.s, 2H, H-6), 3.683 (dd, 1H, J=8.4 Hz, 10.3 Hz, H-2), 3.460 (dd, 1H, J=J=4.1 Hz, 10.2 Hz, H-3), 3.113 (br.d, 1H, H-1), 2.756 (br.ddd, 1H, $NCH_2$), 2.563 (br.ddd, 1H, $NCH_2$), 1.53-1.24 (m, 40H, $20CH_2$), 0.893 (t, 3H, J=7.1 Hz, $CH_3$)

(34) Synthesis of Compound 26

In argon atmosphere, N-ethyldiisopropylamine (322 µl, 20 eq) was added to a dichloroethane solution (3 ml) of Compound 17 (26.7 mg, 0.0922 mmol), and chloromethyl methyl ether (70.1 µl, 10 eq) was added dropwise thereto, followed by stirring at room temperature for 15 minutes and then at 60° C. for 1 day. The reaction solution was ice-cooled, triethylamine (1 ml) was added thereto, and ethanol (1 ml) was added dropwise thereto, followed by stirring at room temperature for 35 minutes. The solvent of the reaction solution was evaporated under reduced pressure, the resulting residue was dissolved in ethyl acetate and washed with saturated sodium bicarbonate water and saturated brine in this order, the resulting organic layer was dried over magnesium sulfate, and the solvent was evaporated under reduced pressure. The resulting residue was purified by silica gel column chromatography (toluene:ethyl acetate=1:1, 0.2% triethylamine) to obtain Compound 26 (34 mg, 97.6%).

Developing solvent of Compound 26 (toluene:ethyl acetate=1:1) Rf: 0.44

$C_{15}H_{27}N_3O_8$ MW: 377.39

$^1$H-NMR (500 MHz, $CDCl_3$)

δ=5.755 (br.s, 1H, H-5a), 4.899, 4.894, 4.854, 4.812, 4.781, 4.729, 4.668, 4.650 (8d, 8H, J=6.6 Hz, 6.6 Hz, 6.6 Hz, 6.4 Hz, 6.6 Hz, 6.6 Hz, 6.4 Hz, 6.6 Hz, $4OCH_2$), 4.203 (br.d, 1H), 4.152 (br.s, 2H), 3.964 (n, 1H), 3.833 (dd, 1H, J=7.1 Hz, 9.0 Hz), 3.701 (dd, 1H, J=7.3 Hz, 9.0 Hz), 3.476, 3.440, 3.380 (3s, 12H, $4OCH_3$)

(35) Synthesis of Compound 27

Water (30 ml) and triphenylphosphine (6.03 g, 2.0 eq) were added to a toluene solution (150 ml) of Compound 26 (4.34 g, 11.5 mmol), followed by stirring at 105° C. for 105 minutes. Toluene and ethanol were added to the reaction solution, evaporation of the solvent under reduced pressure was repeated 3 times, and the resulting residue was purified by silica gel column chromatography (chloroform:methanol=20:1, 0.2% triethylamine) to obtain Compound 27 (3.86 g, 95.5%).

Developing solvent of Compound 27 (chloroform:methanol=10:1) Rf: 0.35 $C_{15}H_{29}NO_g$ MW: 351.39

$^1$H-NMR (500 MHz, $CDCl_3$)

δ=5.743 (br.s, 1H, H-5a), 4.896, 4.854, 4.833, 4.811, 4.765, 4.744, 4.663, 4.644 (8d, 8H, J=6.6 Hz, 6.8 Hz, 6.3 Hz, 6.6 Hz, 6.8 Hz, 6.6 Hz, 6.6 Hz, 6.6 Hz, $4OCH_2$), 4.212 (br.d, 1H), 4.148, 4.078 (2br.d, 2H, H-6a, H-6b), 3.837 (m, 1H), 3.443, 3.439, 3.378 (3s, 12H, $4OCH_3$)

(36) Synthesis of Compound 28

In argon atmosphere, triethylamine (211 µl, 1.515 mmol) was added to a dichloromethane solution (3 ml) of Compound 27 (131.1 mg, 0.379 mmol), followed by ice-cooling, and di-t-butyl dicarbonate (174 µl, 0.758 mmol) was added thereto, followed by stirring for 50 minutes while gradually raising the temperature of the reaction solution to room temperature. The reaction solution was ice-cooled, diluted with ethyl acetate and washed with saturated sodium bicarbonate water and saturated brine in this order, the resulting organic layer was dried over magnesium sulfate, and the solvent was evaporated under reduced pressure. The resulting residue was purified by silica gel column chromatography (toluene:ethyl acetate=3:2, 0.2% triethylamine) to obtain Compound 28 (168.6 mg, 98.6%).

Developing solvent of Compound 28 (toluene:ethyl acetate=1:1) Rf: 0.30

$C_{20}H_{37}NO_{10}$ MW: 451.51

$^1$H-NMR (500 MHz, $CDCl_3$)

δ=5.843 (br.s, 1H, H-5a), 4.982 (d, 1H, J=9.2 Hz, NH), 4.868, 4.790, 4.785, 4.769, 4.736, 4.723, 4.655, 4.633 (8d, 8H, J=6.8 Hz, 6.6 Hz, 7.1 Hz, 6.6 Hz, 6.6 Hz, 6.1 Hz, 6.6 Hz, 6.6 Hz, $4OCH_2$), 4.291 (br.d, 1H), 4.177-4.145 (m, 2H), 4.077 (br.d, 1H), 3.990 (br.dd, 1H), 3.693 (m, 1H), 3.443, 3.422, 3.410, 3.375 (4s, 12H, $4OCH_3$), 1.436 (s, 9H, $CC(CH_3)_3$)

(37) Synthesis of Compound 29-1

In argon atmosphere, a DMF solution (1.5 ml) of Compound 28 (88.2 mg, 0.195 mmol) was ice-cooled, and sodium hydride (60% in oil, 28.1 mg, 0.703 mmol) was added thereto, followed by stirring for 10 minutes under ice-cooling. Then, bromobutane (31.5 µl, 0.293 mmol) was added thereto, followed by stirring for 4 hours while gradually raising the temperature of the reaction solution to room temperature. The reaction solution was ice-cooled, and methanol (1 ml) was added dropwise thereto, followed by stirring for 30 minutes. The reaction solution was diluted with diethyl ether, and saturated sodium bicarbonate water was added thereto, followed by stirring. Then, the organic layer was washed with saturated sodium bicarbonate water and saturated brine in this order and dried over magnesium sulfate, and the solvent was evaporated under reduced pressure. The resulting residue was purified by silica gel column chromatography (toluene:ethyl acetate=10:1, 0.2% triethylamine) to obtain Compound 29-1 (94.4 mg, 95.2%).

Developing solvent of Compound 29-1 (toluene:ethyl acetate=1:1) Rf: 0.63

$C_{24}H_{45}NO_{10}$ MW: 507.61

(38) Synthesis of Compound 30-1

Hydrochloric acid (4 N, 5.0 ml) was added to a THF solution (3.0 ml) of Compound 29-1 (94.4 mg, 0.186 mmol), followed by stirring at room temperature for 1 day. The solvent of the reaction solution was evaporated under reduced pressure, and the resulting residue was azeotroped with ethanol 3 times. The resulting residue was purified by silica gel column chromatography (chloroform:methanol:water=60:35:8). Then, the mixture was dissolved in methanol (0.5 ml)-water (0.5 ml), and 25% aqueous ammonia (0.5 ml) was added thereto. The reaction solution was directly purified by silica gel column chromatography (chloroform:methanol:water=60:35:8) to obtain Compound 30-1 (37.2 mg, 86.5%).

Developing solvent of Compound 30-1 (chloroform:methanol:water 60:35:8) Rf: 0.18

$C_{11}H_{21}NO_4$ MW: 231.29

$^1$H-NMR (500 MHz, $CDCl_3:CD_3OD$=2:1)

δ=5.615 (br.s, 1H, H-5a), 4.194, 4.114 (br.2d, 2H, H-6a, H-6b), 4.156 (m, 1H), 3.553 (dd, 1H, J=7.6 Hz, 10.0 Hz), 3.445 (dd, 1H, J=8.3 Hz, 10.0 Hz), 3.260 (br.d, 1H), 2.781 (br.ddd, 1H, $NCH_2$), 2.590 (br.ddd, 1H, $NCH_2$), 1.55-1.26 (m, 4H, $2CH_2$), 0.950 (t, 3H, J=7.3 Hz, $CH_3$)

(39) Synthesis of Compound 29-2

In argon atmosphere, a DMF solution (3 ml) of Compound 28 (168.6 mg, 0.373 mmol) was ice-cooled, and sodium hydride (60% in oil, 53.8 mg, 1.344 mmol) was added thereto, followed by stirring for 10 minutes under ice-cooling. Then, n-octyl bromide (96.8 μl, 0.560 mmol) was added dropwise thereto, followed by stirring for 3 hours while gradually raising the temperature of the reaction solution to room temperature. The reaction solution was ice-cooled, and methanol (1 ml) was added dropwise thereto, followed by stirring for 30 minutes. The reaction solution was diluted with diethyl ether (200 ml), and saturated sodium bicarbonate water was added thereto, followed by stirring. Then, the organic layer was washed with saturated sodium bicarbonate water and saturated brine in this order and dried over magnesium sulfate, and the solvent was evaporated under reduced pressure. The resulting residue was purified by silica gel column chromatography (toluene:ethyl acetate=3:1, 0.2% triethylamine) to obtain Compound 29-2 (155.1 mg, 73.7%).

Developing solvent of Compound 29-2 (toluene:ethyl acetate=1:1) Rf: 0.57

$C_{28}H_{53}NO_{10}$ MW: 563.72

$^1$H-NMR (500 MHz, Me$_2$SO-d$_6$, 60° C.)

δ=5.460 (br.s, 1H, H-5a), 4.794-4.756 (m, 3H, OCH$_2$), 4.728, 4.688 (2d, 2H, J=6.6 Hz, 6.1 Hz, OCH$_2$), 4,601-4.565 (m, 3H, OCH$_2$), 4.155 (br.d, 1H), 4.056-3.981 (m, 2H), 3.687 (d, 1H, J=7.8 Hz, 9.5 Hz), 3.343, 3.336, 3.269, 3.251 (4s, 12H, 4OCH$_3$), 2.985 (m, 1H, NCH$_2$), 1.53-1.20 (m, 12H, 6CH$_2$), 1.251 (s, 9H, CC(CH$_3$)$_3$), 0.857 (t, 3H, J=7.1 Hz, CH$_3$)

(40) Synthesis of Compound 30-2

Hydrochloric acid (4 N, 6 ml) was added to a THF solution (4 ml) of Compound 29-2 (121 mg, 0.215 mmol), followed by stirring at room temperature for 1 day. The solvent of the reaction solution was evaporated under reduced pressure, and the resulting residue was azeotroped with ethanol 3 times. The resulting residue was purified by Sephadex LH-20 (trade name, manufactured by Pharmacia Biotech) (chloroform:methanol=1:1). Then, the mixture was dissolved in water (0.5 ml), and 25% aqueous ammonia (0.5 ml) was added thereto. The reaction solution was directly purified by silica gel column chromatography (chloroform:methanol:water=60:35:8) to obtain Compound 30-2 (31 mg, 50.20%).

Developing solvent of Compound 30-2 (chloroform:methanol:water=60:35:8) Rf: 0.25

$C_{15}H_{29}NO_4$ MW: 287.40

$^1$H-NMR (500 M CD$_3$OD)

δ=5.639 (br.s, 1H, H-5a), 4.178-4.084 (m, 3H), 3.478 (dd, 1H, J=7.6 Hz, 10.0 Hz), 3.407 (dd, 1H, J=8.5 Hz, 10.0 Hz), 3.206 (br.d, 1H), 2.742 (br.ddd, 1H, NCH$_2$), 2.555 (br.ddd, 1H, NCH$_2$), 1.55-1.27 (m, 12H, 6CH$_2$), 0.900 (t, 3H, J=7.1 Hz, CH$_3$)

(41) Synthesis of Compound 294

In argon atmosphere, a DMF solution (2 ml) of Compound 28 (116.0 mg, 0.257 mmol) was ice-cooled, and sodium hydride (60% in oil, 37 mg, 0.925 mmol) was added thereto, followed by stirring for 10 minutes under ice-cooling. Then, lauryl bromide (92.5 μl, 0.385 mmol) was added dropwise thereto, followed by stirring for 4 hours while gradually raising the temperature of the reaction solution to room temperature. The reaction solution was ice-cooled, and methanol (1 ml) was added dropwise thereto, followed by stirring for 30 minutes. The reaction solution was diluted with diethyl ether, and saturated sodium bicarbonate water was added thereto, followed by stirring. Then, the organic layer was washed with saturated sodium bicarbonate water and saturated brine in this order and dried over magnesium sulfate, and the solvent was evaporated under reduced pressure. The resulting residue was purified by silica gel column chromatography (toluene:ethyl acetate=10:1, 0.2% triethylamine) to obtain Compound 294 (149.8 mg, 94.1%).

Developing solvent of Compound 29-4 (toluene:ethyl acetate=1:1) Rf: 0.66

$C_{32}H_{61}NO_{10}$ MW: 619.83

(42) Synthesis of Compound 30-4

Hydrochloric acid (4 N, 8 ml) was added to a THF solution (5 ml) of Compound 29-4 (149.8 mg, 0.240 mmol), followed by stirring at room temperature for 1 day. The solvent of the reaction solution was evaporated under reduced pressure, and the resulting residue was azeotroped with ethanol 3 times. The resulting residue was purified by silica gel column chromatography (chloroform:methanol:water=60:35:8). Then, the mixture was dissolved in water (0.1 ml)-MeOH (0.5 ml), and 25% aqueous ammonia (0.5 ml) was added thereto. Ten minutes thereafter, the precipitated crystals were collected by filtration to obtain Compound 30-4 (72 mg, 87.3%).

Developing solvent of Compound 30-4 (chloroform:methanol water 60:35:8) Rf: 0.37

$C_{19}H_{37}NO_4$ MW: 343.5

$^1$H-NMR (500 MHz, CDCl$_3$: CD$_3$OD=2:1)

δ=5.612 (br.s, 1H, H-5a), 4.193, 4.103 (br.2d, 2H, H-6a, H-6b), 4.167 (m, 1H), 3.551 (dd, 1H, J 7.8 Hz, 10.0 Hz), 3.417 (dd, 1H, J=8.6 Hz, 10.0 Hz), 3.214 (br.d, 1H), 2.745 (br.ddd, 1H, NCH$_2$), 2.539 (br.ddd, 1H, NCH$_2$), 1.53-1.27 (m, 20H, 10CH$_2$), 0.886 (t, 3H, J=7.1 Hz, CH$_3$)

(43) Synthesis of Compound 29-5

In argon atmosphere, a DMF solution (2 ml) of Compound 28 (134.7 mg, 0.298 mmol) was ice-cooled, and sodium hydride (60% in oil, 42.9 mg, 1.073 mmol) was added thereto, followed by stirring for 10 minutes under ice-cooling. Then, myristyl bromide (133.1 μl, 0.447 mmol) was added dropwise thereto, followed by stirring for 6 hours while gradually raising the temperature of the reaction solution to room temperature. The reaction solution was ice-cooled, and methanol (1 ml) was added dropwise thereto, followed by stirring for 30 minutes. The reaction solution was diluted with diethyl ether, and saturated sodium bicarbonate water was added thereto, followed by stirring. Then, the organic layer was washed with saturated sodium bicarbonate water and saturated brine in this order and dried over magnesium sulfate, and the solvent was evaporated under reduced pressure. The resulting residue was purified by silica gel column chromatography (toluene:ethyl acetate=10:1, 0.2% triethylamine) to obtain Compound 29-5 (172.9 mg, 89.5%).

Developing solvent of Compound 29-5 (toluene:ethyl acetate=1:1) Rf: 0.59

$C_{34}H_{65}NO_{10}$ MW: 647.88

$^1$H-NMR (500 MHz, CDCl$_3$)

δ=5.566 (br.s, 1H, H-5a), 4.921 (br.d, 1H, OCH$_2$), 4.882-4.807 (m, 3H, OCH$_2$), 4.743 (d, 1H, J=6.3 Hz, OCH$_2$), 4.691-4.619 (m, 3H, OCH$_2$), 3.779 (m, 1H), 3,443, 3.433, 3.371, 3.356 (4s, 12H, 4OCH$_3$), 3.064 (m, 1H, NCH$_2$), 1.58-1.25 (m, 24H, 12CH$_2$), 1.256 (s, 9H, CC(CH$_3$)$_3$), 0.881 (t, 3H, J=7.1 Hz, CH$_3$)

(44) Synthesis of Compound 30-5

Hydrochloric acid (4 N, 8.5 ml) was added to a THF solution (5 ml) of Compound 29-5 (172.9 mg, 0.267 mmol), followed by stirring at room temperature for 1 day. The solvent of the reaction solution was evaporated under reduced pressure, and the resulting residue was azeotroped with ethanol 3 times. The resulting residue was purified by silica gel column chromatography (chloroform:methanol:water=60:35:8). Then, the mixture was dissolved in water (0.2 ml), and 25% aqueous ammonia (0.2 ml) was added thereto. Ten minutes thereafter, the precipitated crystals were collected by filtration to obtain Compound 30-5 (32.2 mg, 32.5%).

Developing solvent of Compound 30-5 (chloroform:methanol:water=60:35:88)

Rf: 0.38

$C_{21}H_{41}NO_4$ MW: 371.55

$^1$H-NMR (500 MHz, $CDCl_3$: $CD_3OD$=2:1)

δ=5.609 (br.s, 1H, H-5a), 4.192, 4.103 (br.2d, 2H, H-6a, H-6b), 4.167 (m, 1H), 3.551 (dd, 1H, J=7.6 Hz, 10.0 Hz), 3.424 (t, 1H, J=9.2 Hz), 3.225 (br.d, 1H), 2.753 (br.ddd, 1H, $NCH_2$), 2.550 (br.ddd, 1H, $NCH_2$), 1.53-1.26 (m, 24H, 12$CH_2$), 0.885 (t, 3H, J=7.1 Hz, $CH_3$)

(45) Synthesis of Compound 29-6

In argon atmosphere, a Do solution (1.5 ml) of Compound 28 (100.1 mg, 0.222 mmol) was ice-cooled, and sodium hydride (60% in oil, 32 mg, 0.798 mmol) was added thereto, followed by stirring for 10 minutes under ice-cooling. Then, 1-bromooctadecane (110.9 mg, 0.333 mmol) was added thereto, followed by stirring for 4 hours while gradually raising the temperature of the reaction solution to room temperature. The reaction solution was ice-cooled, and methanol (1 ml) was added dropwise thereto, followed by stirring for 30 minutes. The reaction solution was diluted with diethyl ether, and saturated sodium bicarbonate water was added thereto, followed by stirring. The organic layer was washed with saturated sodium bicarbonate water and saturated brine in this order and dried over magnesium sulfate, and the solvent was evaporated under reduced pressure. The resulting residue was purified by silica gel column chromatography (toluene:ethyl acetate=8:1, 0.2% triethylamine) to obtain Compound 29-6 (111.6 mg, 71.5%).

Developing solvent of Compound 29-6 (toluene:ethyl acetate=1:1) Rf: 0.60

$C_{38}H_{73}NO_{10}$ MW: 703.99

$^1$H-NMR (500 MHz, $CDCl_3$)

δ=5.566 (br.s, 1H, H-5a), 4.923 (br.d, 1H, $OCH_2$), 4.883-4.806 (m, 3H, $OCH_2$), 4.743 (d, 1H, J=6.6 Hz, $OCH_2$), 4.658-4.618 (m, 3H, $OCH_2$), 3.762 (m, 1H), 3.443, 3.356 (2s, 12H, 4$OCH_3$), 3.064 (m, 1H, $NCH_2$), 1.61-1.26 (m, 32H, 16$CH_2$), 1.255 (s, 9H, CC($CH_3$)$_3$), 0.880 (t, 3H, J=7.1 Hz, $CH_3$)

(46) Synthesis of Compound 30-6

Hydrochloric acid (4 N, 4 ml) was added to a THF solution (2.5 ml) of Compound 29-6 (81.9 mg, 0.116 mmol), followed by stirring at room temperature for 1 day, and further stirring at 35° C. for 2 hours. The solvent of the reaction solution was evaporated under reduced pressure, and the resulting residue was azeotroped with ethanol 3 times. The resulting residue was purified by silica gel column chromatography (chloroform:methanol:water=60:35:8). Then, the mixture was dissolved in methanol (0.5 ml)-water (0.5 ml), and 25% aqueous ammonia (0.5 ml) was added thereto. Ten minutes thereafter, the thus precipitated crystals were collected by filtration to obtain Compound 30-6 (54 mg, 79.8%).

Developing solvent of Compound 30-6 (chloroform:methanol:water=60:35:8) Rf: 0.30

$C_{25}H_{49}NO_4$ MW: 427.66

$^1$H-NMR (500 MHz, $CDCl_3$: $CD_3OD$=2:1)

δ=5.609 (br.s, 1H, H-5a), 4.192, 4.101 (br.2d, 2H, H-6a, H-6b), 4.170 (m, 1H), 3.553 (dd, 1H, J=7.6 Hz, 10.0 Hz), 3.415 (dd, 1H, J=8.5 Hz, 10.0 Hz), 3.211 (br.d, 1H), 2.743 (br.ddd, 1H, $NCH_2$), 2.536 (br.ddd, 1H, $NCH_2$), 1.53-1.23 (m, 32H, 16$CH_2$), 0.885 (t, 3H, J=7.0 Hz, $CH_3$)

(47) Synthesis of Compound 29-7

In argon atmosphere, a DMF solution (1.5 ml) of Compound 28 (80 mg, 0.177 mmol) was ice-cooled, and sodium hydride (60% in oil, 25.5 mg, 0.638 mmol) was added thereto, followed by stirring for 10 minutes under ice-cooling. Then, bromodocosane (103.5 mg, 0.266 mmol) was added thereto, followed by stirring for 2 hours while gradually raising the temperature of the reaction solution to room temperature. The reaction solution was ice-cooled, and methanol (1 ml) was added dropwise thereto, followed by stirring for 30 minutes. The reaction solution was diluted with diethyl ether, and saturated sodium bicarbonate water was added thereto, followed by stirring. Then, the organic layer was washed with saturated sodium bicarbonate water and saturated brine in this order and dried over magnesium sulfate, and the solvent was evaporated under reduced pressure. The resulting residue was purified by silica gel column chromatography (toluene:ethyl acetate=10:1, 0.2% triethylamine) to obtain Compound 29-7 (39.5 mg, 29.4%).

Developing solvent of Compound 29-7 (toluene:ethyl acetate=1:1) Rf: 0.56

$C_{42}H_{81}NO_{10}$ MW: 760.10

(48) Synthesis of Compound 30-7

Hydrochloric acid (4 N, 1.5 ml) was added to a THF solution (1.0 ml) of Compound 29-7 (39.5 mg, 0.052 mmol), followed by stirring at 40° C. for 1 day. The solvent of the reaction solution was evaporated under reduced pressure, and the resulting residue was azeotroped with ethanol 3 times. The resulting residue was purified by silica gel column chromatography (chloroform:methanol:water=60:35:8). Then, the mixture was dissolved in methanol (0.5 ml)-water (0.5 ml), and 25% aqueous ammonia (0.5 ml) was added thereto. Ten minutes thereafter, the thus precipitated crystals were collected by filtration to obtain Compound 30-7 (25 mg, 99%)

Developing solvent of Compound 30-7 (chloroform:methanol:water=60:35:8) Rf: 0.30

$C_{29}H_{57}NO_4$ MW: 483.77

$^1$H-NMR (500 MHz, $CDCl_3$: $CD_3OD$=2:1)

δ=5.609 (br.s, 1H, H-5a), 4.192, 4.102 (br.2d, 2H, H-6a, H-6b), 4.167 (m, 1H), 3.553 (dd, 1H, J=7.8 Hz, 10.0 Hz), 3.416 (dd, 1H, J=8.3 Hz, 10.0 Hz), 3.212 (br.d, 1H), 2.744 (br.ddd, 1H, $NCH_2$), 2.537 (br.ddd, 1H, $NCH_2$), 1.53-1.26 (m, 40H, 20$CH_2$), 0.886 (t, 3H, J=7.1 Hz, $CH_3$)

<2> Synthesis of Substances of the Invention (1) Synthesis of Substance A-1 of the Invention Compound 25-1 (16.5 mg, 0.0713 mmol) was suspended in 3 ml of water, and 0.5 ml of concentrated hydrochloric acid was added thereto, followed by stirring for 1 hour. Then, the mixture was evaporated for drying under reduced pressure at 50° C., and ethanol and toluene were added thereto to carry out azeotropy 3 times. The residue was dissolved in water and freeze-dried to obtain Substance A-1 of the invention (14.7 mg, 77%) as a colorless solid.

$^1$H-NMR (500 MHz, $CD_3OD$)

δ=5.731 (br.d, 1H, H-5a), 4.259 (br.d, 1H, H-6a), 4.165 (d, 1H, J=4.0 Hz, H-1), 4.146 (br.d, 1H, H-6b), 3.947 (dd, 1H, J=8.1, 9.8 Hz, H-3), 3.691 (br.d, 1H, H-4), 3.543 (dd, 1H J=4.21, 9.8 Hz, H-2), 3.094 (br.ddd, 2H, H-1'), 1.74-1.28 (m, 4H, 2$CH_2$), 1.008 (t, 3H, J=7.3 Hz, $CH_3$)

(2) Synthesis of Substance A-2 of the Invention

Compound 25-2 (51.3 mg) was suspended in 12 ml of water, and 0.2 ml of concentrated hydrochloric acid was added thereto, followed by stirring for 5 minutes. Then, the mixture was evaporated at 50° C., and ethanol and toluene were added thereto to carry out azeotropy 3 times. The residue was dissolved in water and freeze-dried to obtain Substance A-2 of the invention (51.7 mg) as a colorless solid.

Melting point; 80.9-82.3° C.

$[\alpha]^{20}{}_D$=+9.83° (c=1.0 methanol)

$^1$H-NMR (500 MHz, 1:2=CD$_3$OD: CDCl$_2$)

δ=5.734 (br.d, 1H, H-5a), 4.268 (brd, 1H, H-6a), 4.153 (d, 1H, J=4.1 Hz, H-1), 4.133 (br.d, 1H, H-6b), 3.953 (dd, 1H, J=8.1, 9.8 Hz, H-3), 3.638 (br.d, 1H, H-4), 3.549 (dd, 1H, J=4.1, 9.8 Hz, H-2), 3.063 (m, 2H, H-1'×2), 1.75, 1.26 (m, 12H, 6CH$_2$, H-2'-7'), 0.894 (t, 3H, J=7.1 Hz, CH$_3$, H-8')

(3) Synthesis of Substance A-3 of the Invention

Compound 25-3 (15.0 mg, 0.0476 mmol) was suspended in 10 ml of water, and 0.5 ml of concentrated hydrochloric acid was added thereto, followed by stirring for 1 hour. Then, the mixture was evaporated at 50° C., and ethanol and toluene were added thereto to carry out azeotropy 3 times. The residue was dissolved in water and freeze-dried to obtain Substance A-3 of the invention (16.7 mg, 99%) as a colorless solid.

$^1$H-NMR (500 M CD$_3$OD)

δ=5.737 (br.d, 1H, H-5a), 4.255 (br.d, 1H, H-6a), 4.165 (d, 1H, J=4.2 Hz, H-1), 4.145 (br.d, 1H, H-6b), 3.950 (dd, 1H, J=8.3, 9.8 Hz, H-3), 3.696 (br.d, 1H, H-4), 3.543 (dd, 1H, J=4.0, 9.8 Hz, H-2), 3.088 (br.ddd, 2H, H-1'), 1.76-1.29 (m, 16H, 8CH$_2$), 0.894 (t, 3H, J=7.1 Hz, CH$_3$)

(4) Synthesis of Substance A-4 of the Invention

Compound 25-4 (15.0 mg, 0.0437 mmol) was suspended in 10 ml of water, and 0.5 ml of concentrated hydrochloric acid was added thereto, followed by stirring for 1 hour. Then, the mixture was evaporated at 50° C., and ethanol and toluene were added thereto to carry out azeotropy 3 times. The residue was dissolved in water and freeze-dried to obtain Substance A-4 of the invention (16.6 mg, 100%) as a colorless solid.

$^1$H-NMR (500 MHz, CD$_3$OD)

δ=5.730 (br.d, 1H, H-5a), 4.255 (br.d, 1H, H-6a), 4.163 (d, 1H, J=3.9 Hz, H-1), 4.144 (br.d, 1H, H-6b), 3.942 (dd, 1H, J=8.3, 9.8 Hz, H-3), 3.690 (br.d, 1H, H-4), 3.540 (dd, 1H, J=3.9, 9.8 Hz, H-2), 3.086 (br.ddd, 2H, H-1'), 1.75-1.29 (m, 20H, 10CH$_2$), 0.893 (t, 3H, J=7.1 Hz, CH$_3$)

(5) Synthesis of Substance A-5 of the Invention

Compound 25-5 (15.0 mg, 0.0404 mmol) was suspended in 10 ml of water, and 0.5 ml of concentrated hydrochloric acid was added thereto, followed by stirring for 1 hour. Then, the mixture was evaporated at 50° C., and ethanol and toluene were added thereto to carry out azeotropy 3 times. The residue was dissolved in water and freeze-dried to obtain Substance A-5 of the invention (7.2 mg, 44%) as a colorless solid.

$^1$H-NMR (500 MHz, CD$_3$OD)

δ=5.723 (br.d, 1H, H-5a), 4.252 (br.d, 1H, H-6a), 4.159 (d, 1H, J=4.7 Hz, H-1), 4.141 (br.d, 1H, H-6b), 3.933 (dd, 1H, J=8.1, 9.8 Hz, H-3), 3.683 (br.d, 1H, H-4), 3.532 (dd, 1H, J=4.0, 9.8 Hz, H-2), 3.082 (br.ddd, 2H, H-1'), 1.74-1.28 (m, 24H 12CH$_2$), 0.893 (t, 3H, J=7.1 Hz, CH$_3$)

(6) Synthesis of Substance A-6 of the Invention

Compound 25-6 (13.2 mg, 0.0309 mmol) was suspended in 10 ml of water, and 0.5 ml of concentrated hydrochloric acid was added thereto, followed by stirring for 1 hour. Then, the mixture was evaporated at 50° C., and ethanol and toluene were added thereto to carry out azeotropy 3 times. The residue was dissolved in water and freeze-dried to obtain Substance A-6 of the invention (14.3 mg, 99%) as a colorless solid.

$^1$H-NMR (500 MHz, CD$_3$OD)

δ=5.708 (br.d, 1H, H-5a), 4.259 (br d, 1H, H-6a), 4.159 (d, 1H, J=4.2 Hz, H-1), 4.142 (br.d, 1H, H-6b), 3.925 (dd, 1H, J=8.3, 9.8 Hz, H-3), 3.670 (br d, 1H, H-4), 3.533 (dd, 1H, J=3.9, 9.8 Hz, H-2), 3.080 (br.ddd, 2H, H-1'), 1.74-1.28 (m, 32H, 16CH$_2$), 0.892 (t, 3H, J=7.1 Hz, CH$_3$)

(7) Synthesis of Substance A-7 of the Invention

Compound 25-7 (13.5 mg, 0.0279 mmol) was suspended in 10 ml of water, and 0.5 ml of concentrated hydrochloric acid was added thereto, followed by stirring for 1 hour. Then, the mixture was evaporated at 50° C., and ethanol and toluene were added thereto to carry out azeotropy 3 times. The residue was dissolved in water and freeze-dried to obtain Substance A-7 of the invention (14.5 mg, 100%) as a colorless solid.

$^1$H-NM (500 MHz, CD$_3$OD)

δ=5.710 (br.d, 1H, H-5a), 4.255 (br.d, 1H, H-6a), 4.157 (d, 1H, J=4.2 Hz, H-1), 4.140 (br.d, 1H, H-6b), 3.924 (dd, 1H, J=8.3, 9.8 Hz, H-3), 3.675 (br.d, 1H, H-4), 3.529 (dd, 1H, J=4.2, 9.8 Hz, H-2), 3.081 (br.ddd, 2H, H-1'), 1.74-1.25 (m, 40H, 20CH$_2$), 0.893 (t, 3 H, J=7.1 Hz, CH$_3$)

(8) Synthesis of Substance B-1 of the Invention

Compound 30-1 (15 mg, 0.0649 mmol) was suspended in 10 ml of water, and 0.5 ml of concentrated hydrochloric acid was added thereto, followed by stirring for 1 hour. Then, the mixture was evaporated at 50° C., and ethanol and toluene were added thereto to carry out azeotropy 3 times. The residue was dissolved in water and freeze-dried to obtain Substance B-1 of the invention (16 mg, 92%) as a colorless solid.

$^1$H-NMR (500 MHz, CD$_3$OD)

δ=5.672 (br.s, 1H, H-5a), 4.250, 4.190 (2br.d, 2H, H-6a, H-6b), 4.124 (m, 1H, H-1), 3.814 (m, 1H, H-4), 3.691 (dd, 1H, J=8.8, 9.9 Hz, H-3), 3.533 (dd, 1H, J=8.1, 9.8 Hz, H-2), 3.106 (t, 2H, J=8.1 Hz, H-1'a, H-1'b), 1.75-1.27 (m, 4H, 2CH$_2$), 1.005 (t, 3H, J=7.3 Hz, CH$_3$)

(9) Synthesis of Substance B-2 of the Invention

Compound 30-2 (22.4 mg, 0.0780 mmol) was suspended in 8 ml of water and mixed with 1.0 ml of concentrated hydrochloric acid, followed by stirring for 1 hour. Then, the mixture was evaporated at 50° C., and ethanol and toluene were added thereto to carry out azeotropy 3 times. The residue was dissolved in water and freeze-dried to obtain Substance B-2 of the invention (18.3 mg, 72%) as a colorless solid.

$^1$H-NMR (500 MHz, CD$_3$OD)

δ=5.659 (br.s, 1H, H-5a), 4.250, 4.138 (2br.d, 2H, H-6a, H-6b), 4.105 (m, 1H, H-1), 3.802 (m, 1H, H-4), 3.656 (dd, 1H, J=8.8, 9.8 Hz, H-3), 3.515 (dd, 1H, J=7.9, 9.9 Hz, H-2), 3.089 (t, 2H, J=8.1 Hz, H-1'a, H-1'b), 1.73-1.31 (m, 12H, 6CH$_2$), 0.905 (t, 3H, J=7.0 Hz, CH$_3$)

(10) Synthesis of Substance B-4 of the Invention

Compound 30-4 (15 mg, 0.0437 mmol) was suspended in 10 ml of water, and 0.5 ml of concentrated hydrochloric acid was added thereto, followed by stirring for 1 hour. Then, the mixture was evaporated at 50° C., and ethanol and toluene were added thereto to carry out azeotropy 3 times. The residue was dissolved in water and freeze-dried to obtain Substance B-4 of the invention (I 5 mg, 90%) as a colorless solid.

$^1$H-NMR (500 MHz, CD$_3$OD)

δ=5.658 (br.s, 1H, H-5a), 4.251, 4.188 (2br.d, 2H, H-6a, H-6b), 4.117 (m, 1H, H-1), 3.800 (m, 1H, H-4), 3.676 (dd, 1H, J=8.8, 9.8 Hz, H-3), 3.528 (dd, 1H, J=7.8, 9.8 Hz, H-2), 3.090 (t, 2H, J=8.1 Hz, H-1'a, H-1'b), 1.76-1.28 (m, 20H, 10CH$_2$), 0.892 (t, 3H, J=7.1 Hz, CH$_3$)

(11) Synthesis of Substance B-5 of the Invention

Compound 30-5 (15 mg, 0.0404 mmol) was suspended in 10 ml of water, and 0.5 ml of concentrated hydrochloric acid was added thereto, followed by stirring for 1 hour. Then, the mixture was evaporated at 50° C., and ethanol and toluene were added thereto to carry out azeotropy 3 times. The residue was dissolved in water and freeze-dried to obtain Substance B-5 of the invention (16 mg, 97%) as a colorless solid.

$^1$H-NMR (500 MHz, CD$_3$OD)

δ=5.652 (brs, 1H, H-5a), 4.253, 4.192 (2br.d, 2H, H-6a, H-6b), 4.121 (m, 1H, H-1), 3.794 (m, 1H, H-4), 3.679 (t, 1H, J=9.8 Hz, H-3), 3.533 (dd, 1H, J=8.1, 9.8 Hz, H-2), 3.087 (t, 2H, J=8.1 Hz, H-1'a, H-1'b), 1.74-1.27 (m, 24H, 12CH$_2$), 0.891 (t, 3H, J=7.1 Hz, CH$_3$)

(12) Synthesis of Substance 13-6 of the Invention

Compound 30-6 (15 mg, 0.0351 mmol) was suspended in 10 ml of water, and 0.5 ml of concentrated hydrochloric acid was added thereto, followed by stirring for 1 hour. Then, the mixture was evaporated at 50° C., and ethanol and toluene were added thereto to carry out azeotropy 3 times. The residue was dissolved in water and freeze-dried to obtain Substance B-6 of the invention (14 mg, 86%) as a colorless solid.

$^1$H-NMR (500 MHz, CD$_3$OD)

δ=5.647 (br.s, 1H, H-5a), 4.254, 4.186 (2br.d, 2H, H-6a, H-6b), 4.110 (m, 1H, H-1), 3.793 (m, 1H, H-4), 3.661 (t, 1H, J=9.8 Hz, H-3), 3.524 (dd, 1H, J=7.8, 9.8 Hz, H-2), 3.085 (t, 2H, J=8.1 Hz, H-1'a, H-1'b), 1.74-1.27 (m, 32H, 16CH$_2$), 0.892 (t, 3H, J=7.1 Hz, CH$_3$)

(13) Synthesis of Substance B-7 of the Invention

Compound 30-7 (15 mg, 0.0310 mmol) was suspended in 10 ml of water, and 0.5 ml of concentrated hydrochloric acid was added thereto, followed by stirring for 1 hour. Then, the mixture was evaporated at 50° C., and ethanol and toluene were added thereto to carry out azeotropy 3 times. The residue was dissolved in water and freeze-dried to obtain Substance B-7 of the invention (16 mg, 99%) as a colorless solid.

$^1$H-NMR (500 MHz, CD$_3$OD)

δ=5.643 (br.s, 1H, H-5a), 4.257, 4.185 (2br.d, 2H, H-6a, H-6b), 4.108 (m, 1H, H-1), 3.792 (m, 1H, H-4), 3.651 (t, 1H, J=9.8 Hz, H-3), 3.521 (dd, 1H, J=7.8, 10.0 Hz, H-2), 3.084 (t, 2H, J=8.1 Hz, H-1'a, H-1'b), 1.73-1.27 (m, 40H, 20CH$_2$), 0.893 (t, 3H, J=7.1 Hz, CH$_3$)

<3> Measurement of Neutral β-galactosidase Inhibitory Activity

Figure 2:
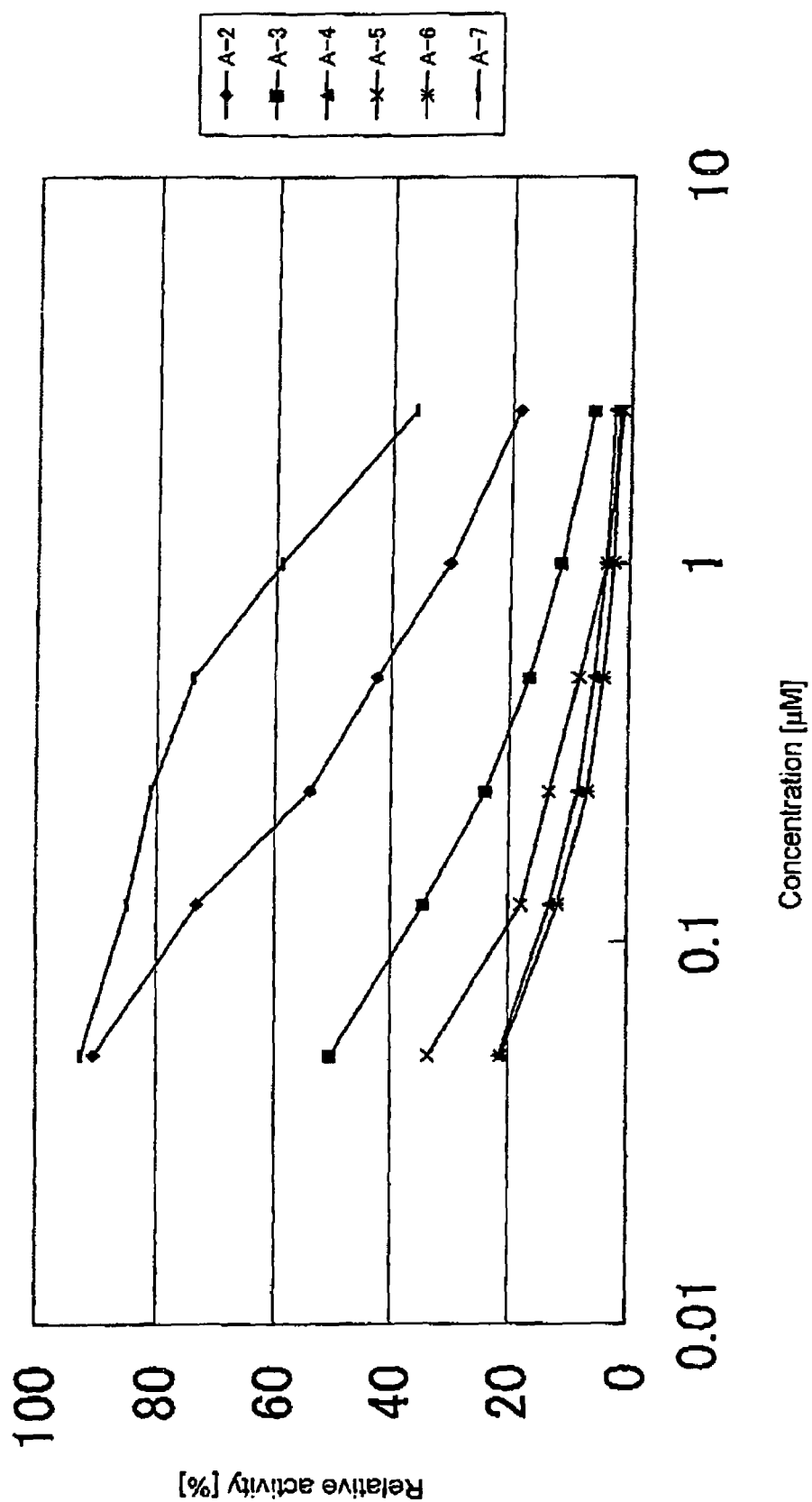
FIG. 2 is a graph showing neutral β-galactosidase inhibitory activity of Substances A-2 to 7 of the invention.
Figure 3:
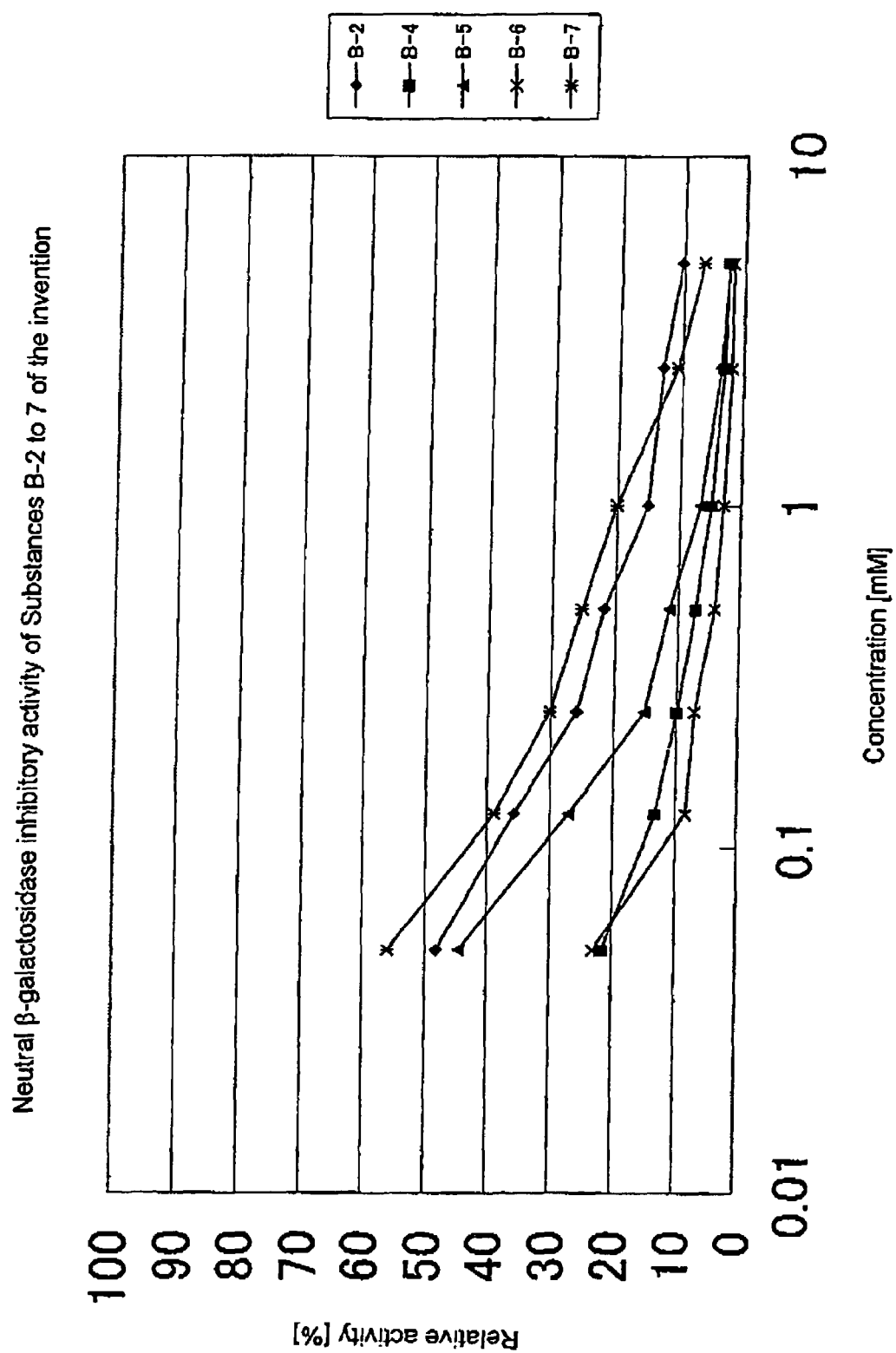
FIG. 3 is a graph showing neutral β-galactosidase inhibitory activity of Substances B-2 to 7 of the invention.

Each of Substances A-2 to 7 and B-2 to 7 of the invention dissolved in water for injection, to which DMSO had been added and dissolved therein, if necessary, was diluted with 0.02 M HEPES buffer (pH 7.3) to give a concentration of 0.05, 0.125, 0.25, 0.5, 1.0, 2.5 or 5.0 μM and added at 25 μl into a 96 well microplate. Then, a 0.02 M HEPES buffer (pH 7.3) solution of bovine liver derived β-D-galactosidase (manufactured by Sigma) was added at 25 μl, 4-methylumbelliferyl-β-D-galactopyranoside (10 μM) was further added as a fluorescence substrate at 50 μl, followed by incubation at 37° C. for 30 minutes. Then, the reaction was stopped by adding 100 μl of 2 M Na$_2$CO$_3$. An amount of 4-methylumbelliferone released by the enzyme reaction (fluorescence intensity) was measured (excitation wavelength 355 nm, measuring wavelength 460 nm) by a fluorescence reader (product name: ARVOSX manufactured by WALLAC). An amount of the 4-methylumbelliferone released at the time of not adding the inhibitor was defined as 100%, and quantitative change in the 4-methylumbelliferone formed by addition of each substance to be evaluated was relatively evaluated. Results of Substances A-2 to 7 of the invention are shown in FIG. 2, and results of Substances B-2 to 7 of the invention in FIG. 3. In addition, as the 50% inhibition concentration (IC$_{50}$ value), concentration of each substance of the invention which reduces 50% of the concentration of 4-methylumbelliferone at the time of un-adding each substance of the invention was calculated from an inhibition curve.

In this connection, regarding those which have high inhibitory activity among the substances of the invention, their IC$_{50}$ values were calculated by carrying out the enzyme inhibition measurement by further diluting them to a concentration of 0.0025, 0.005, 0.01 or 0.025 μM. The results are shown in Table 3.

TABLE 3

| Substances of the invention | 50% Inhibition concentration (IC$_{50}$ value, μM) |
|---|---|
| Substance A-2 | 0.377 |
| Substance A-3 | 0.0499 |
| Substance A-4 | 0.014 (*) |
| Substance A-5 | 0.005 (*) |
| Substance A-6 | 0.025 (*) |
| Substance A-7 | 1.402 |
| Substance B-2 | 0.096 (*) |
| Substance B-4 | <0.005 (*) |
| Substance B-5 | 0.006 (*) |
| Substance B-6 | 0.017 (*) |
| Substance B-7 | 0.067 |

(*) Measured to 0.0025, 0.005, 0.01 and 0.025 μM

<4> Measurement of Acidic β-galactosidase Inhibitory Activity

Figure 4:
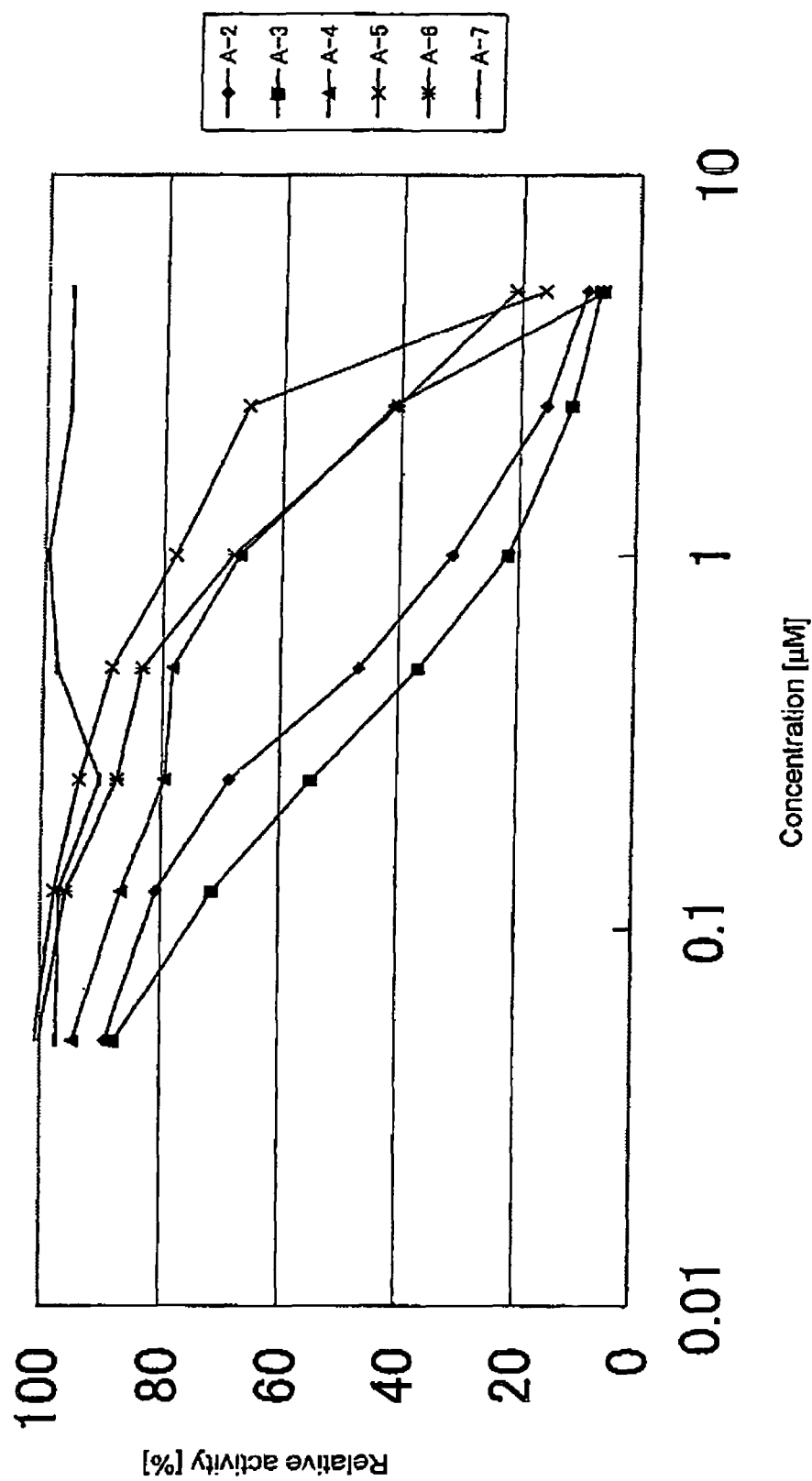
FIG. 4 is a graph showing acidic β-galactosidase inhibitory activity of Substances A-2 to 7 of the invention.

Each of Substances A-2 to 7 of the invention dissolved in water for injection, to which DMSO had been added and dissolved therein, if necessary, was diluted with a 0.2 M acetate buffer (pH 4.4) to give a concentration of 0.05, 0.125, 0.25, 0.5, 1.0, 2.5 or 5.0 μM and added at 25 μl into a 96 well microplate. Then, a 0.2 M acetate buffer (pH 4.4) solution of bovine sperm-derived β-D-galactosidase (manufactured by Signa) was added at 25 μl, and 4-methylumbelliferyl-β-D-galactopyranoside (10 μM) was further added as a fluorescence substrate at 50 μl, followed by incubation at 25° C. for 30 minutes. Then, the reaction was stopped by adding 100 μl of 2 M Na$_2$CO$_3$, and an amount of 4-methylumbelliferone released by the enzyme reaction (fluorescence intensity) was measured (excitation wavelength 355 nm, measuring wavelength 460 nm) by a fluorescence reader (product name; ARVOSX manufactured by WALLAC). An amount of the 4-methylumbelliferone released at the time of not adding the inhibitor was defined as 100%, and quantitative change in the 4-methylumbelliferone formed by addition of each substance to be evaluated was relatively evaluated. The results are shown in FIG. 4. In addition, as the 50% inhibition concentration (IC$_{50}$ value), the concentration of each substance of the invention which reduces 50% of the concentration of 4-methylumbelliferone at the time of un-adding each substance of the invention was calculated from an inhibition curve. The results are shown in Table 4.

TABLE 4

| Substances of the invention | 50% Inhibition concentration (IC$_{50}$ value, μM) |
|---|---|
| Substance A-2 of the invention | 0.476 |
| Substance A-3 of the invention | 0.301 |
| Substance A-4 of the invention | 1.432 |
| Substance A-5 of the invention | 2.689 |
| Substance A-6 of the invention | 1.791 |
| Substance A-7 of the invention | — |

<5> Measurement of Neutral β-glucosidase Inhibitory Activity

Figure 5:
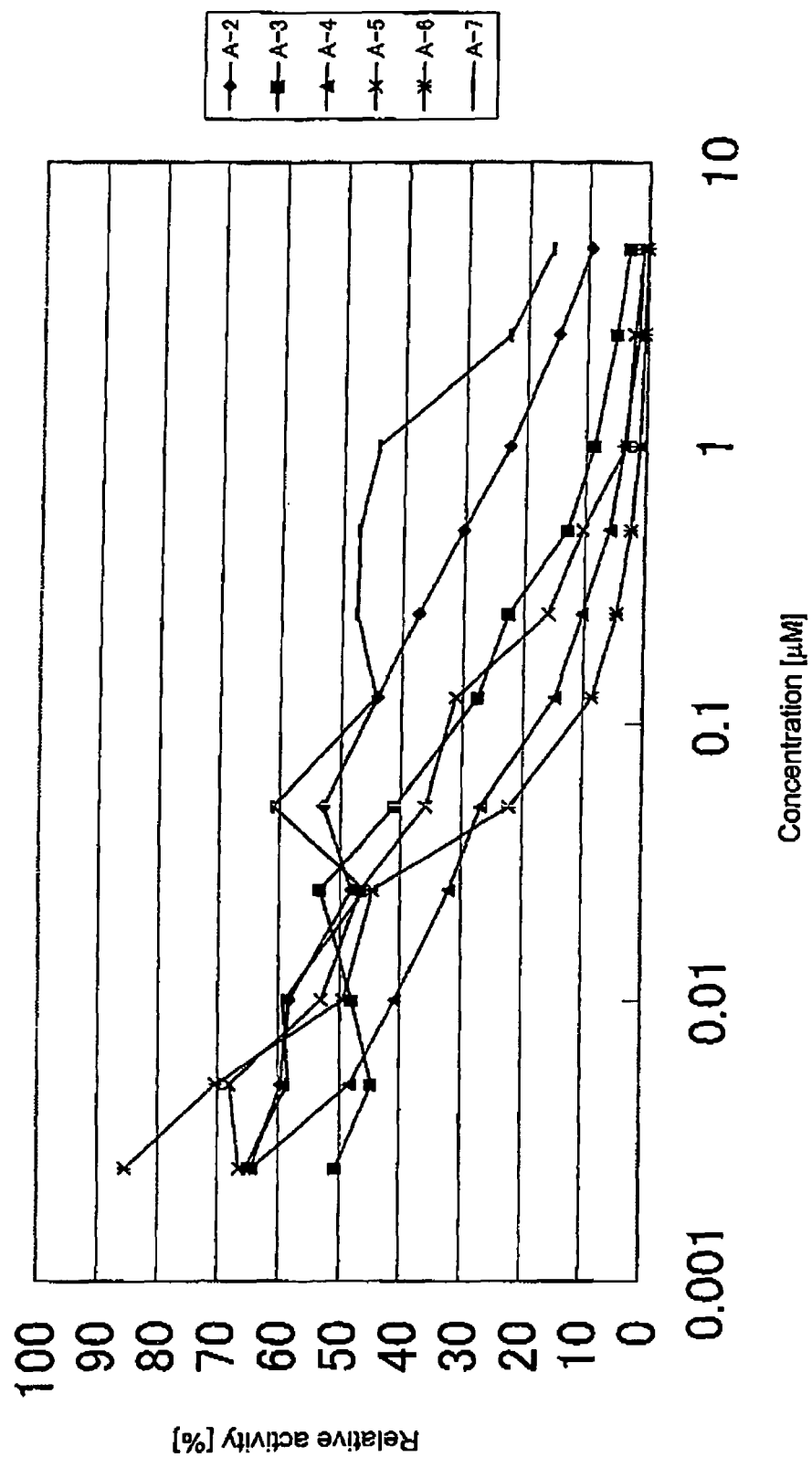
FIG. 5 is a graph showing neutral β-glucosidase inhibitory activity of Substances A-2 to 7 of the invention.
Figure 6:
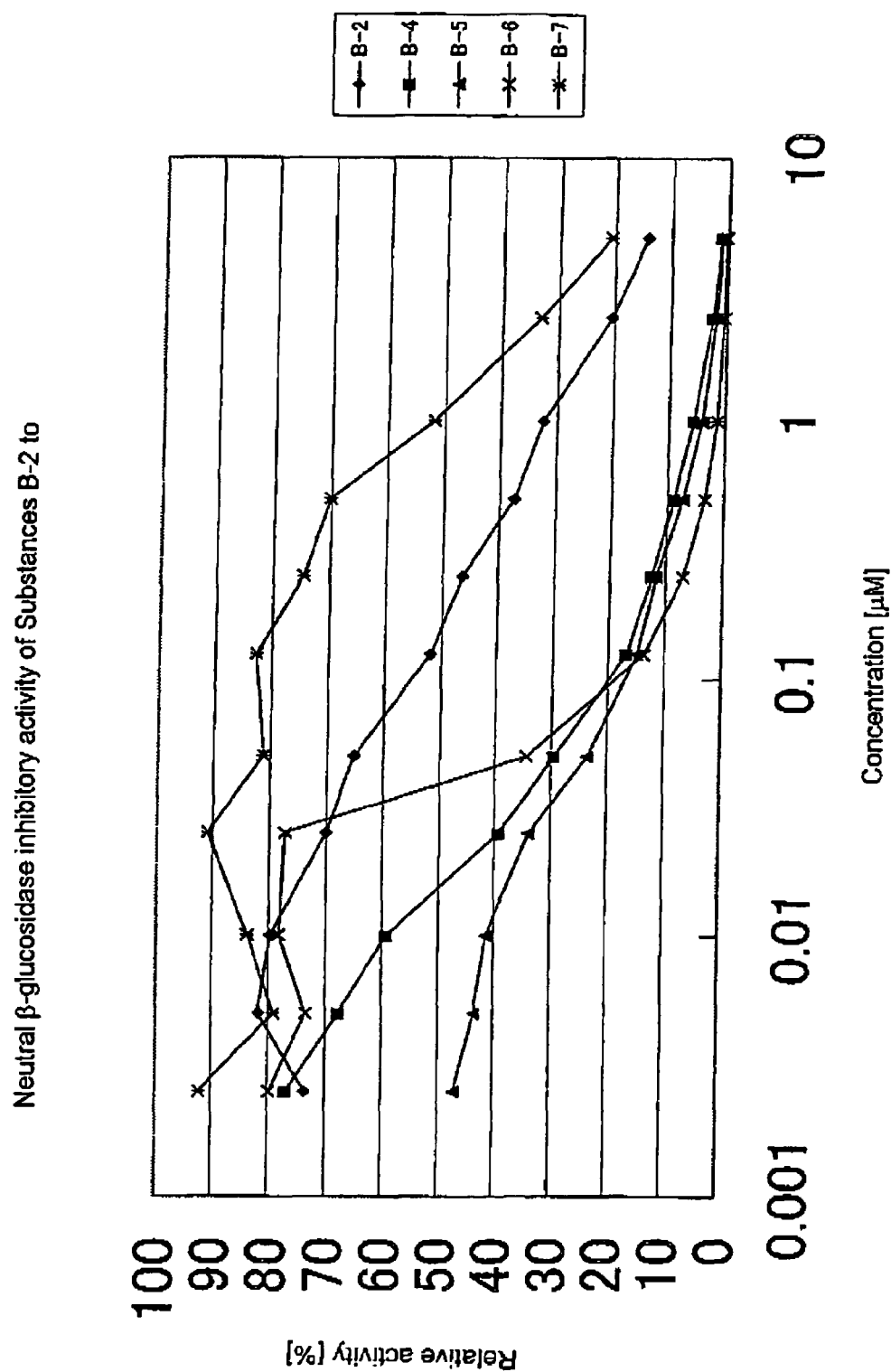
FIG. 6 is a graph showing neutral β-glucosidase inhibitory activity of Substances B-2 to 7 of the invention.
Figure 7:
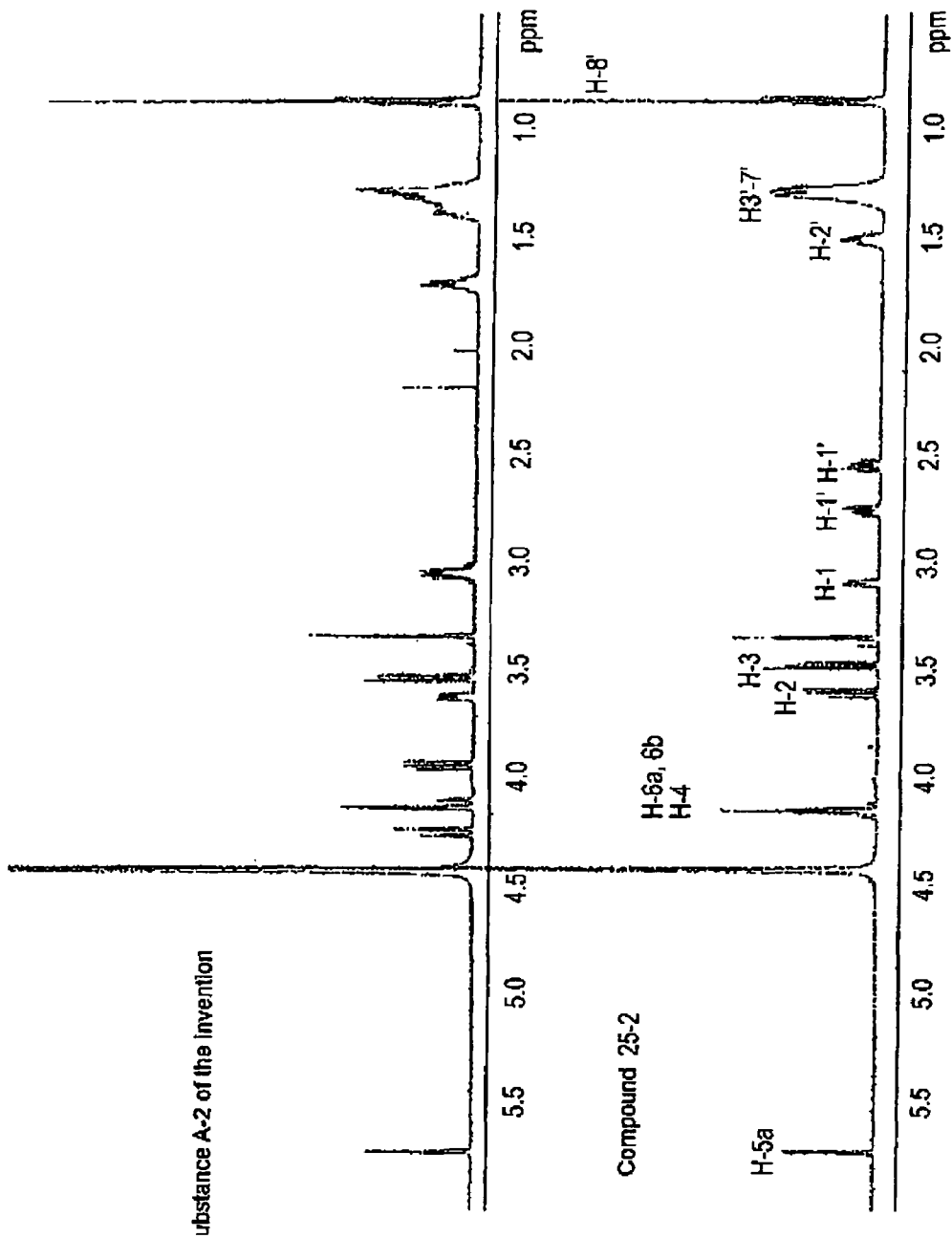
FIG. 7 is a graph showing $^1$H-NMR charts of 25-2 and Substance A-2 of the invention.

Each of Substances A-2 to 7 and B-2 to 7 of the invention dissolved in water for injection, to which DMSO had been added and dissolved therein, as occasion demands, was diluted with 0.02 M HEPES buffer (pH 7.3) to give a concentration of 0.0025, 0.005, 0.01, 0.025, 0.05, 0.125, 0.25, 0.5, 1.0, 2.5 or 5.0 μM and added at 25 μl into a 96 well microplate. Then, a 0.02 M HEPES buffer (pH 7.3) solution of bovine liver-derived β-D-galactosidase (manufactured by Sigma) was added at 25 μl, and 4-methylumbelliferyl-β-D-galactopyranoside (10 μM) was further added as a fluorescence substrate at 50 μl, followed by incubation at 37° C. for 30 minutes. Then, the reaction was stopped by adding 100 μl of 2 M $Na_2CO_3$, and an amount of 4-methylumbelliferone released by the enzyme reaction (fluorescence intensity) was measured (excitation wavelength 355 nm, measuring wavelength 460 nm) by a fluorescence reader (product name: ARVOSX, manufactured by WALLAC). An amount of the 4-methylumbelliferone released at the time of not adding the inhibitor was defined as 100%, and quantitative change in the 4-methylumbelliferone formed by addition of each substance to be evaluated was relatively evaluated. Results of Substances A-2 to 7 of the invention are shown in FIG. 5, and results of Substances B-2 to 7 of the invention in FIG. 6. In addition, as the 50% inhibition concentration ($IC_{50}$ value), the concentration of each substance of the invention which reduces 50% of the concentration of 4-methylumbelliferone at the time of un-adding each substance of the invention was calculated from an inhibition curve. The results are shown in Table 5.

TABLE 5

| Substances of the invention | 50% Inhibition concentration ($IC_{50}$ value, μM) |
| --- | --- |
| Substance A-2 | 0.028 |
| Substance A-3 | 0.007 |
| Substance A-4 | 0.006 |
| Substance A-5 | 0.014 |
| Substance A-6 | 0.013 |
| Substance A-7 | 0.059 |
| Substance B-2 | 0.152 |
| Substance B-4 | 0.015 |
| Substance B-5 | <0.003 |
| Substance B-6 | 0.033 |
| Substance B-7 | 1.043 |

<6> Solubility Test

When solubility of Substance A-2 of the invention was confirmed, it dissolved in distilled water at a concentration of 300 mg/ml and 24° C. On the other hand, Compound 25-2 was not dissolved in water at a concentration of 2 mg/ml and 24° C. and dissolved at 40° C., but Compound 25-2 precipitated when returned again to 24° C.

In addition, the solubility of Compound 30-2 and the substance B-2 of the invention was confirmed by adding 50 μl of distilled water to 5.4 mg of each sample at 19° C. Substance B-2 of the invention was completely dissolved when 50 μl of distilled water was added (>108 mg/ml). On the other hand, Compound 30-2 was not dissolved by addition of 50 μl of distilled water, and completely dissolved when 1.95 ml of the same was added (2.8 mg/ml).

While the invention has been describe in detail and with reference to specific embodiments thereof, it will be apparent to one skilled in the art that various changes and modifications can be made therein without departing from the spirit and scope of the invention.

This application is based on a Japanese patent application filed on May 19, 2003 (Japanese Patent Application No. 2003-140868), entire contents thereof being thereby incorporated by reference.

INDUSTRIAL APPLICABILITY

Acid addition salts of novel carba-sugar amine derivatives having inhibitory activity upon β-galactosidase or β-glucosidase and with improved solubility are provided by the invention. In addition, the above-described acid addition salts of novel carba-sugar amine derivatives can be used for the excellent treatment or prevention of glycolipid metabolic disorders based on the β-galactosidase or β-glucosidase gene.

What is claimed is:

1. An acid addition salt of a carba-sugar amine derivative of formula (1):

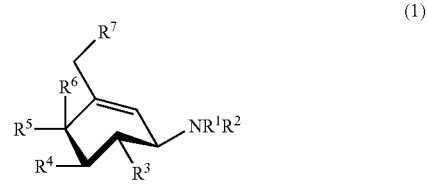

(1)

wherein $R^1$ and $R^2$ each independently is a hydrogen atom, or an alkyl group, an alkenyl group, an alkynyl group, an acyl group, an aryl group or an aralkyl group which may have one or two of the following substituents (I) or (II), or $R^1$ and $R^2$ are taken together to be a substituent (III):

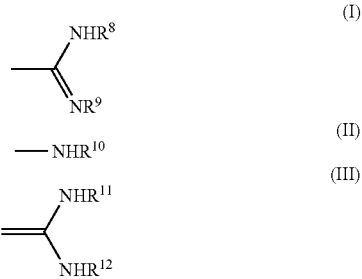

wherein $R^8$ to $R^{12}$ each independently is an alkyl group, an alkenyl group, an alkynyl group, an acyl group, an aryl group or an aralkyl group;

with the proviso that both $R^1$ and $R^2$ are not a hydrogen atom at the same time;

$R^3$, $R^4$ and $R^7$ each independently is a hydroxyl group or a hydroxyl group having a substituent; and $R^5$ and $R^6$ each independently is a hydrogen atom, a hydroxyl group or a hydroxyl group having a substituent, with the proviso that when one of $R^5$ and $R^6$ is a hydrogen atom, the other is a hydroxyl group or a hydroxyl group having a substituent, wherein the hydroxyl group having a substituent at positions $R^3$-$R^7$ is a hydroxyl group where the hydrogen of the hydroxyl group is replaced with a substituent selected from the group consisting of an aralkyl group, a silyl group, an alkanoyl group, an aroyl group, an alkoxyalkyl group, and a aralkyloxyalkyl group or wherein two hydroxyl groups at positions $R^3$-$R^7$ together form a substituent selected from the group consisting of an alkylidene group, an isopropylidene group, and an aralkylidene group,
wherein said salt of a carba-sugar amine derivative is a hydrochloride or sulfate salt.

2. An acid addition salt of a carba-sugar amine derivative of formula (1)-A-2:

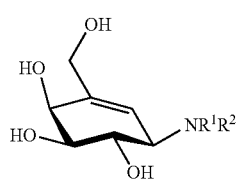

(1)-A-2 wherein R¹ and R² each is as defined in claim 1.

3. An acid addition salt of a carba-sugar amine derivative of (1)-B-2:

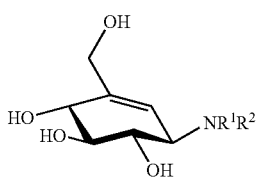

(1)-B-2 wherein R¹ and R² each is as defined in claim 1.

4. The acid addition salt of a carba-sugar amine derivative according to claim 1, which is hydrochloride.

5. A composition comprising the acid addition salt of a carba-sugar amine derivative according to claim 1 and a pharmaceutically acceptable carrier.

6. A method of treating a glycolipid metabolic disorder in a mammal in need thereof, comprising administering the composition according to claim 5 to said mammal in an amount sufficient to deliver an effective amount of said acid addition salt of a carba-sugar amine derivative.

7. The acid addition salt of a carba-sugar amine derivative according to claim 2, which is hydrochloride or sulfate.

8. The acid addition salt of a carba-sugar amine derivative according to claim 3, which is hydrochloride or sulfate.

9. A composition comprising the acid addition salt of a carba-sugar amine derivative according to claim 2 and a pharmaceutically acceptable carrier.

10. A method of treating a glycolipid metabolic disorder in a mammal in need thereof, comprising administering the composition according to claim 9 to said mammal in an amount sufficient to deliver an effective amount of said acid addition salt of a carba-sugar amine derivative.

11. The method of claim 10, wherein said mammal is a human.

12. The method of claim 10, wherein said effective amount ranges from 0.1 µg to 1000 mg per day.

13. The method of claim 10, wherein said administering is oral or parenteral.

14. A composition comprising the acid addition salt of a carba-sugar amine derivative according to claim 3 and a pharmaceutically acceptable carrier.

15. A method of treating a glycolipid metabolic disorder in a mammal in need thereof, comprising administering the composition according to claim 14 to said mammal in an amount sufficient to deliver an effective amount of said acid addition salt of a carba-sugar amine derivative.

16. The method of claim 15, wherein said mammal is a human.

17. The method of claim 15, wherein said effective amount ranges from 0.1 µg to 1000 mg per day.

18. The method of claim 15, wherein said administering is oral or parenteral.

19. A composition comprising the acid addition salt of a carba-sugar amine derivative according to claim 4 and a pharmaceutically acceptable carrier.

20. A method of treating a glycolipid metabolic disorder in a mammal in need thereof, comprising administering the composition according to claim 19 to said mammal in an amount sufficient to deliver an effective amount of said acid addition salt of a carba-sugar amine derivative.

21. The method of claim 20, wherein said mammal is a human.

22. The method of claim 20, wherein said effective amount ranges from 0.1 µg to 1000 mg per day.

23. The method of claim 20, wherein said administering is oral or parenteral.

24. The method of claim 6, wherein said mammal is a human.

25. The method of claim 6, wherein said effective amount ranges from 0.1 µg to 1000 mg per day.

26. The method of claim 6, wherein said administering is oral or parenteral.

27. The acid addition salt of a carba-sugar amine derivative according to claim 1, which is sulfate.

* * * * *